(12) United States Patent
Lee et al.

(10) Patent No.: US 11,666,276 B2
(45) Date of Patent: Jun. 6, 2023

(54) METHOD FOR PROCESSING BIOMETRIC SIGNAL, AND DETACHABLE WEARABLE ELECTRONIC DEVICE AND STORAGE MEDIUM FOR THE SAME

(71) Applicant: Samsung Electronics Co., Ltd., Gyeonggi-do (KR)

(72) Inventors: Suho Lee, Gyeonggi-do (KR); Younghyun Kim, Gyeonggi-do (KR); Jeongmin Park, Gyeonggi-do (KR); Seongmin Je, Gyeonggi-do (KR); Shinhee Cho, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 275 days.

(21) Appl. No.: 16/951,083

(22) Filed: Nov. 18, 2020

(65) Prior Publication Data
US 2021/0186420 A1    Jun. 24, 2021

(30) Foreign Application Priority Data
Dec. 24, 2019    (KR) ........................ 10-2019-0174491

(51) Int. Cl.
*A61B 5/00*    (2006.01)
*H04B 1/3827*    (2015.01)

(52) U.S. Cl.
CPC ............ *A61B 5/681* (2013.01); *A61B 5/0006* (2013.01); *H04B 1/385* (2013.01); *G06F 2218/12* (2023.01)

(58) Field of Classification Search
CPC .......... A61B 5/681; A61B 5/0006; A61B 5/24; A61B 5/25; G06K 9/00536; H04B 1/385
See application file for complete search history.

(56) References Cited

U.S. PATENT DOCUMENTS

| | | | |
|---|---|---|---|
| 5,368,041 A * | 11/1994 | Shambroom | G16Z 99/00 128/901 |
| 10,986,465 B2 * | 4/2021 | Patel | H04W 4/027 |
| 2016/0228025 A1 | 8/2016 | Dusan | |
| 2017/0011210 A1 * | 1/2017 | Cheong | A61B 5/681 |
| 2017/0172452 A1 | 6/2017 | Lee et al. | |
| 2017/0273584 A1 | 9/2017 | Huang et al. | |
| 2018/0256104 A1 | 9/2018 | Jeong | |
| 2019/0239769 A1 * | 8/2019 | Lee | A61B 5/282 |
| 2019/0307402 A1 * | 10/2019 | Yamada | A61B 5/296 |

* cited by examiner

*Primary Examiner* — Linda C Dvorak
*Assistant Examiner* — Abigail Bock
(74) *Attorney, Agent, or Firm* — Cha & Reiter, LLC

(57) ABSTRACT

A wearable electronic device and method are disclosed, including: at least one sensor including a plurality of electrodes, at least one processor operatively connected with the at least one sensor, and a memory operatively connected with the at least one processor. The processor implements the method, including detecting coupling of the wearable electronic device with an external accessory contacting a body of a user, and based on detecting the coupling with the external accessory, measuring a biometric signal using a voltage received from at least two electrodes from among a plurality of measurement electrodes included in the external accessory.

20 Claims, 19 Drawing Sheets

METHOD FOR PROCESSING BIOMETRIC SIGNAL, AND DETACHABLE WEARABLE ELECTRONIC DEVICE AND STORAGE MEDIUM FOR THE SAME

CROSS-REFERENCE TO RELATED APPLICATION(S)

This application is based on and claims priority under 35 U.S.C. 119 to Korean Patent Application No. 10-2019-0174491, filed on Dec. 24, 2019, in the Korean Intellectual Property Office, the disclosure of which is herein incorporated by reference in its entirety.

BACKGROUND

Field

Certain embodiments relate to portable devices for measuring biometric signals, and, more particularly, to a wearable device interoperable with a detachable accessory device to detect biometrics.

Description of Related Art

Recently, the use of portable electronic devices such as smart phones, tablet PCs, wearable electronic devices, etc. is increasing, and as electronic technology has advanced, technology for measuring biometric signals has developed as well. In particular, technology has developed that allows continuous monitoring of a user's biometric signals via an electronic device routinely worn by the user, such as a wearable electronic device. The electronic device may include various sensors capable of sensing the user's biometric signals and provide various health-care functions via the sensors. For example, various types of biometric signals may be monitored, including electrical signals, such as electrocardiography (ECG) and electromyogram (EMG), physical signals, such as blood pressure, body temperature, and photoplethysmogram (PPG), and composition-related signals, such as blood glucose level, oxygen saturation, and body composition.

SUMMARY

Among the above-enumerated biometric signals, electrical signals, such as electrocardiogram signals, are detected through electrodes in contact with skin. Therefore, in order to accurately and periodically measure the electrocardiogram, it may be important to accurately place and attach sensor electrodes to the body. For example, it may be desirable to monitor all ECG signals with electrodes that remain worn for a span of 24 to 72 hours.

When the first lead (lead I) formed by both arms is worn and measured, and, the ECG signal of the first lead may allow detection of a degree of atrial fibrillation in tachycardia, bradycardia, and arrhythmia. In addition, although certain symptoms may appear temporarily, measurements are often limited to be performed but once for a short period of time, and may thus miss detection of certain important symptoms, such as irregular atrial activity.

Furthermore, the wearable electronic device may measure biometric signals only while worn on the user's wrist, and depending on the contact state of the contacting electrode, detection of biometrics may be unstable, resulting in reduced accuracy and reliability during ECG monitoring. Therefore, a need exists for increasing measurement accuracy and preventing error that occurs due to contact failure or intermittence between the sensors and the skin.

A wearable electronic device is disclosed, including: at least one sensor including a plurality of electrodes, at least one processor operatively connected with the at least one sensor, a memory operatively connected with the at least one processor, wherein the memory stores instructions executable by the at least one processor to cause the wearable electronic device to: detect coupling of the wearable electronic device with an external accessory contacting a body of a user, and based on detecting the coupling with the external accessory, measure a biometric signal using a voltage received from at least two electrodes from among a plurality of measurement electrodes included in the external accessory.

A method for processing a biometric signal in a wearable electronic device, including: detecting a coupling of the wearable electronic device with an external accessory contacting a body of a user, and based on detecting the coupling with the external accessory, measuring a biometric signal using a voltage received from at least two measurement electrodes from among a plurality of measurement electrodes included in the external accessory.

There is provided a storage medium storing instructions, Other aspects, advantages, and salient features of the disclosure will become apparent to those skilled in the art from the following detailed description, which, taken in conjunction with the annexed drawings, discloses example embodiments of the disclosure.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, wherein.

Throughout the drawings, like reference numerals will be understood to refer to like parts, components, and structures.

DETAILED DESCRIPTION

Hereinafter, various example embodiments of the disclosure will be disclosed with reference to the accompanying drawings.

The terms as used herein are provided merely to describe various example embodiments thereof, but not to limit the embodiments of the disclosure. It is to be understood that the singular forms "a", "an" and "the" include plural references unless the context clearly dictates otherwise. All terms including technical and scientific terms used herein have the same meaning as commonly understood by one of ordinary skill in the art to which the embodiments of the disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the disclosure.

Figure 1A:
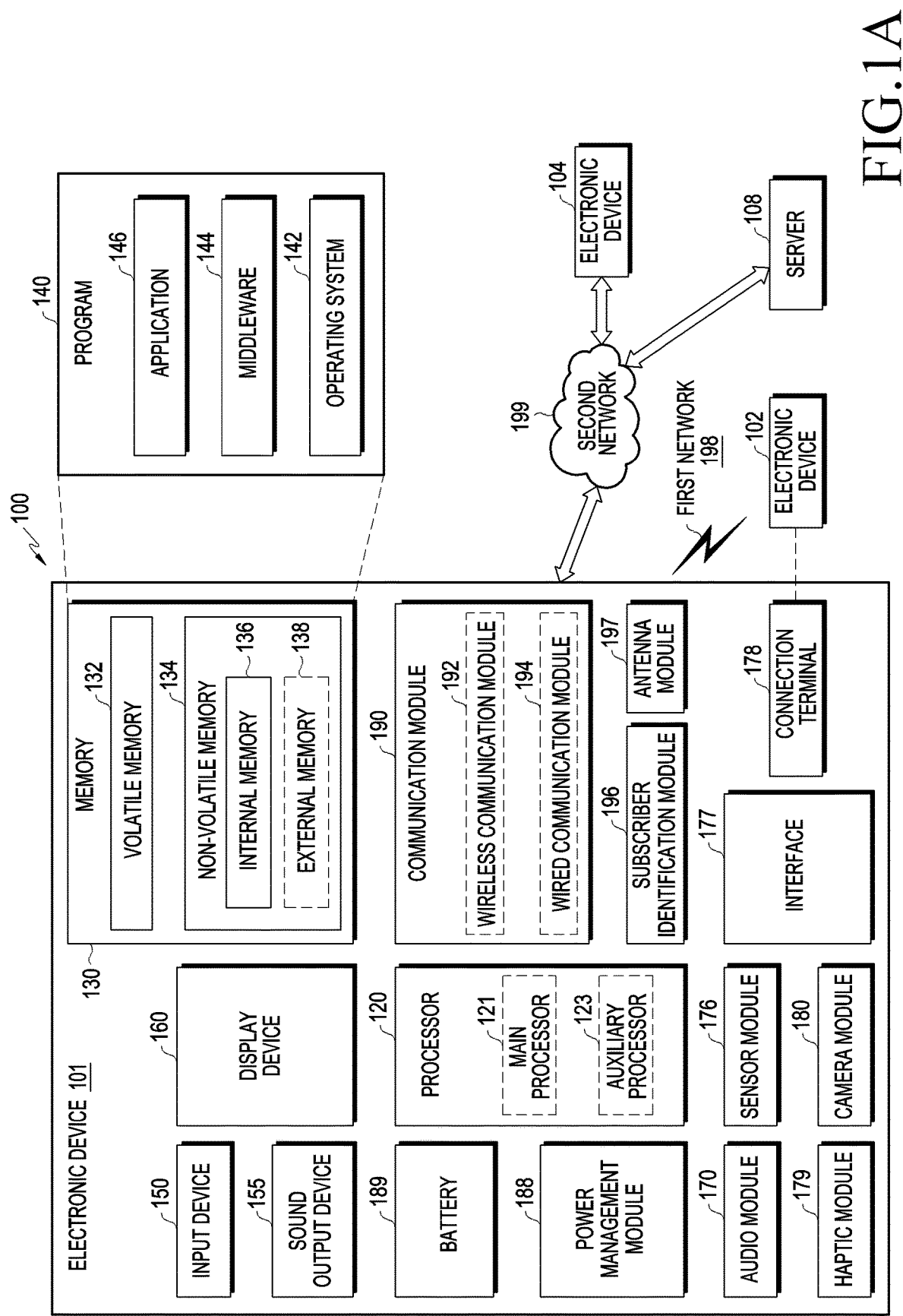
FIG. 1A is a block diagram illustrating an electronic device in a network environment according to an embodiment.

FIG. 1A is a block diagram illustrating an electronic device 101 in a network environment 100 according to certain embodiments. Referring to FIG. 1A, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device). According to an embodiment, the antenna module may include one antenna including a radiator formed of a conductor or conductive pattern formed on a substrate (e.g., a printed circuit board (PCB)). According to an embodiment, the antenna module 197 may include a plurality of antennas. In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 1B:
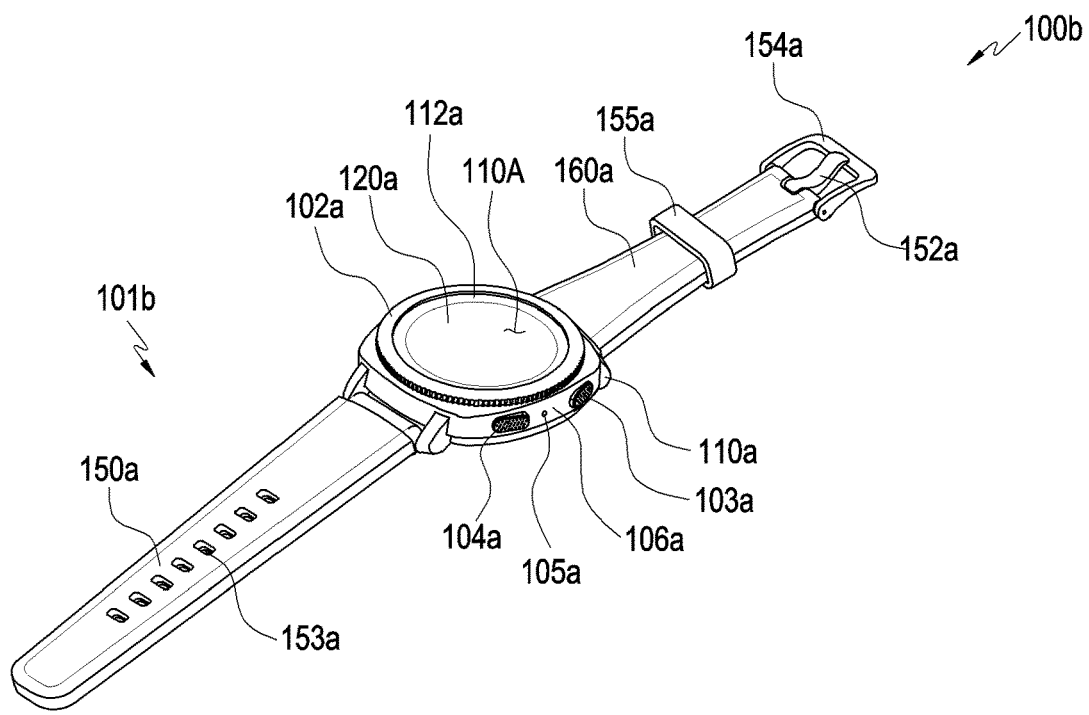
FIG. 1B is a front perspective view illustrating an electronic device according to an embodiment.
Figure 1C:
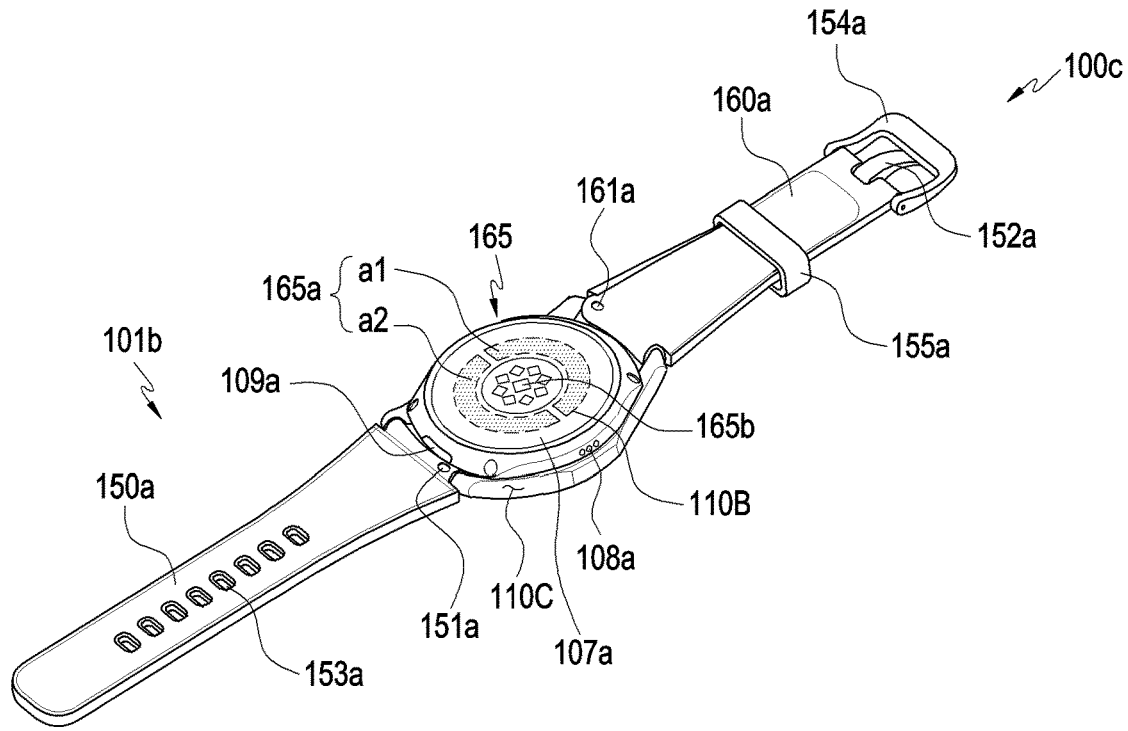
FIG. 1C is a rear perspective view illustrating an electronic device as shown in FIG. 1B.

FIG. 1B is a front perspective view 100b illustrating an electronic device according to an embodiment. FIG. 1C is a rear perspective view 100c illustrating an electronic device as shown in FIG. 1B.

Referring to FIGS. 1B and 1C, according to an embodiment, the wearable device 101b (e.g., the electronic device 101 of FIG. 1A) may include a housing 110a having a first surface (or front surface) 110A, a second surface (or rear surface) 110B, and a side surface 110C surrounding the space between the first surface 110A and the second surface 110B and coupling members 150a and 160a connected to at least part of the housing 110a and configured to allow the electronic device 101b to be detachably worn on the user's body portion (e.g., his wrist or ankle). According to another embodiment (not shown), the housing may denote a structure forming part of the first surface 110A, the second surface 110B, and the side surface 110C of FIGS. 1B and 1C. According to an embodiment, at least part of the first surface 110A may have a substantially transparent front plate 112a (e.g., a glass plate or polymer plate including various coat layers). The second surface 110B may be formed of a substantially opaque rear plate 107a. According to an embodiment, when the electronic device 101b includes a sensor module 165 disposed on the second surface 110B, the rear plate 107a may at least partially include a transparent region. The rear plate 107a may be formed of, e.g., laminated or colored glass, ceramic, polymer, metal (e.g., aluminum, stainless steel (STS), or magnesium), or a combination of at least two thereof. The side surface 110C may be formed by a side bezel structure (or a "side member") 106a that couples to the front plate 112a and the rear plate 107a and includes a metal and/or polymer. According to an embodiment, the rear plate 107a and the side bezel structure 106a may be integrally formed together and include the same material (e.g., a metal, such as aluminum). The coupling members 150a and 160a may be formed of various materials in various shapes. A uni-body structure or multiple unit links which is flexible may be formed of fabric, leather, rubber, urethane, metal, ceramic, or a combination of at least two thereof.

According to an embodiment, the electronic device 101b may include at least one or more of a display 120a, audio modules 105a and 108a, a sensor module 165, key input devices 102a, 103a, and 104a, and a connector hole 109a. According to an embodiment, the electronic device 101b may exclude at least one (e.g., the key input devices 102a, 103a, and 104a, connector hole 109a, or sensor module 165) of the components or may add other components.

According to an embodiment, the electronic device 101b may include a plurality of electrodes for measuring a biometric signal. At least one of the plurality of electrodes may be placed in at least one of the position of the key input device 102a, 103a, or 104a, the position of the bezel 106a, or the position of the display 120a or the housing 110a. Among the key input devices, the wheel key 102a may include a rotary bezel. The display 120a may be exposed through a substantial portion of, e.g., the front plate 112a. The display 120a may have a shape corresponding to the shape of the front plate 112a, e.g., a circle, ellipse, or polygon. The display 120a may be coupled with, or disposed adjacent, a touch detection circuit, a pressure sensor capable of measuring the strength (pressure) of touches, and/or fingerprint sensor.

According to an embodiment, the display 120a may include at least one transparent electrode for measuring biometric signals among the plurality of electrodes for measuring biometric signals.

The audio modules 105a and 108a may include a microphone hole and a speaker hole (operatively coupled with the audio modules 105a and 108a). The microphone hole may have a microphone inside to obtain external sounds. According to an embodiment, there may be a plurality of microphones to be able to detect the direction of a sound. The speaker hole may be used for an external speaker or a receiver for phone talks. According to an embodiment, a speaker may be included without the speaker hole (e.g., a piezo speaker).

The sensor module 165 may generate an electrical signal or data value corresponding to an internal operating state or an external environmental state of the electronic device 101b. The sensor module 165 may include a biometric sensor (e.g., an HRM sensor), and can be placed on the second surface 110B of the housing 110a. The sensor module 165 may further include an electrocardiogram (ECG) sensor 165a, including at least two electrodes a1 and a2 for ECG measurement, and a photoplethysmogram (PPG) sensor 165b for heartrate measurement. The electronic device 101b may further include sensor modules beyond those shown, such as for example at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 102a, 103a, and 104a may include a wheel key 102a disposed on the first surface 110A of the housing 110a to be rotatable in at least one direction and/or side key buttons 103a and 104a disposed on the side surface 110C of the housing 110a. The wheel key 102a may have a shape corresponding to the shape of the front plate 112a. According to an embodiment, the electronic device 101b may exclude all or some of the above-mentioned key input devices 102a, 103a, and 104a and the excluded key input devices 102a, 103a, and 104a may be implemented in other forms, e.g., as soft keys on the display 120a. The connector hole 109a may receive a connector (e.g., a universal serial bus (USB) connector) for transmitting and receiving power and/or data to/from an external electronic device. Another connector hole (not shown) may be included for receiving a connector for transmitting and receiving audio signals to/from the external electronic device. The electronic device 101b may further include a connector cover (not shown) to cover at least part of, e.g., the connector hole 109a and preventing undesirable materials from entering the connector hole.

The coupling members 150a and 160a may detachably be fastened to at least portions of the housing 110a via locking members 151a and 161a. The locking members 151a and 161a may include components or parts for coupling, such as pogo pins, and, according to an embodiment, may be replaced with protrusions or recesses formed on/in the coupling members 150a and 160a. For example, the coupling members 150a and 160a may be coupled in such a manner as to be fitted into or over the recesses or protrusions formed on the housing 110a. The coupling members 150a and 160a may include one or more of a fastening member 152a, fastening member coupling holes 153a, a band guide member 154a, and a band fastening ring 155a.

The fastening member 152a may be configured to allow the housing 110a and the coupling members 150a and 160a to be fastened to the user's body portion (e.g., wrist or ankle). The fastening member coupling holes 153a may fasten the housing 110a and the coupling members 150a and 160a to the user's body portion, corresponding to the fastening member 152a. The band guide member 154a may be configured to restrict movement of the fastening member 152a to a certain range when the fastening member 152a fits into one of the fastening member coupling holes 153a, thereby allowing the coupling members 150a and 160a to be tightly fastened onto the user's body portion. The band fastening ring 155a may limit the range of movement of the coupling members 150a and 160a, with the fastening member 152a fitted into one of the fastening member coupling holes 153a.

Figure 1D:
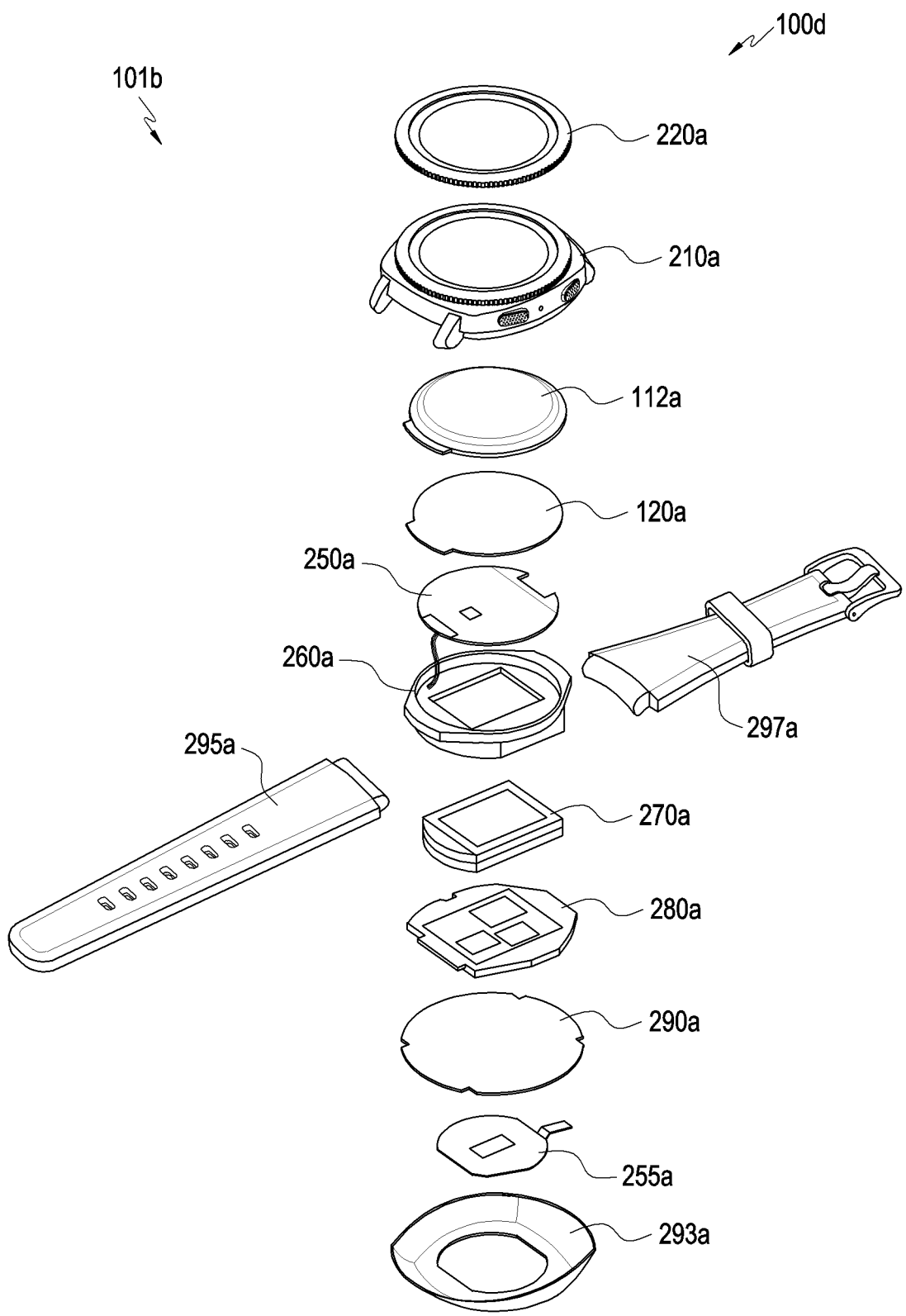
FIG. 1D is an exploded perspective view illustrating an electronic device as shown in FIG. 1B.

FIG. 1D is an exploded perspective view 100d illustrating the electronic device 101b of FIG. 1B.

Referring to FIG. 1D, an electronic device 101b (e.g., the electronic device 101 of FIG. 1A) may include a side bezel structure 210a, a wheel key 220a, a front plate 112a, a display 120a, a first antenna 250a, a second antenna 255a, a supporting member 260a (e.g., a bracket), a battery 270a, a printed circuit board 280a, a sealing member 290a, a rear plate 293a, and coupling members 295a and 297a. At least one of the components of the electronic device 101b may be the same or similar to at least one of the components of the electronic device 101b of FIG. 1A or 1C and no duplicate description is made below. The supporting member 260a may be disposed inside the electronic device 101b to be connected with the side bezel structure 210a or integrated with the side bezel structure 210a. The supporting member 260a may be formed of, e.g., a metal and/or non-metallic material (e.g., polymer). The display 120a may be joined onto one surface of the supporting member 260a, and the printed circuit board 280a may be joined onto the opposite surface of the supporting member 260a. A processor, memory, and/or interface may be mounted on the printed circuit board 280a. The processor may include one or more of, e.g., a central processing unit, an application processor, a graphic processing unit (GPU), a sensor processor, or a communication processor.

The memory may include, e.g., a volatile or non-volatile memory. The interface may include, e.g., a high definition multimedia interface (HDMI), a universal serial bus (USB) interface, a secure digital (SD) card interface, and/or an audio interface. The interface may electrically or physically connect, e.g., the electronic device 101b with an external electronic device and may include a USB connector, an SD card/multimedia card (MMC) connector, or an audio connector.

The battery 270a may be a device for supplying power to at least one component of the electronic device 101b. The battery 270a may include, e.g., a primary cell which is not rechargeable, a secondary cell which is rechargeable, or a fuel cell. At least a portion of the battery 270a may be disposed on substantially the same plane as the printed circuit board 280a. The battery 270a may be integrally or detachably disposed inside the electronic device 101b.

The first antenna 250a may be disposed between the display 120a and the supporting member 260a. The first antenna 250a may include an antenna, e.g., a near-field communication (NFC) antenna, a wireless charging antenna, and/or a magnetic secure transmission (MST) antenna. The first antenna 250a may perform short-range communication with an external device, wirelessly transmit/receive power utilized for charging, or transmit magnetic-based signals including payment data or short-range communication signals. According to an embodiment, an antenna structure may be formed by a portion or combination of the side bezel structure 210a and/or the supporting member 260a.

The second circuit board 255a may be disposed between the circuit board 280a and the rear plate 293a. The second circuit board 255a may include an antenna, e.g., a near-field communication (NFC) antenna, a wireless charging antenna, and/or a magnetic secure transmission (MST) antenna. The second circuit board 255a may perform short-range communication with an external device, wirelessly transmit/receive power for charging, or transmit magnetic-based signals including payment data or short-range communication signals. According to an embodiment, an antenna structure may be formed by a portion or combination of the side bezel structure 210a and/or the rear plate 293a. According to an embodiment, when the electronic device 101b (e.g., the electronic device 101b of FIG. 1B or 1C) includes a sensor module (e.g., the sensor module 165 of FIG. 1B), a sensor element (e.g., a photoelectric conversion element or electrode pad) separate from the second circuit board 255a or the sensor circuit disposed on the second circuit board 255a may be disposed. For example, an electronic component provided as the sensor module 165 may be disposed between the circuit board 280a and the rear plate 293a.

The sealing member 290a may be positioned between the side bezel structure 210a and the rear plate 293a. The sealing member 290a may be configured to block moisture or foreign bodies that may enter the space surrounded by the side bezel structure 210a and the rear plate 293a, from the outside.

Figure 2:
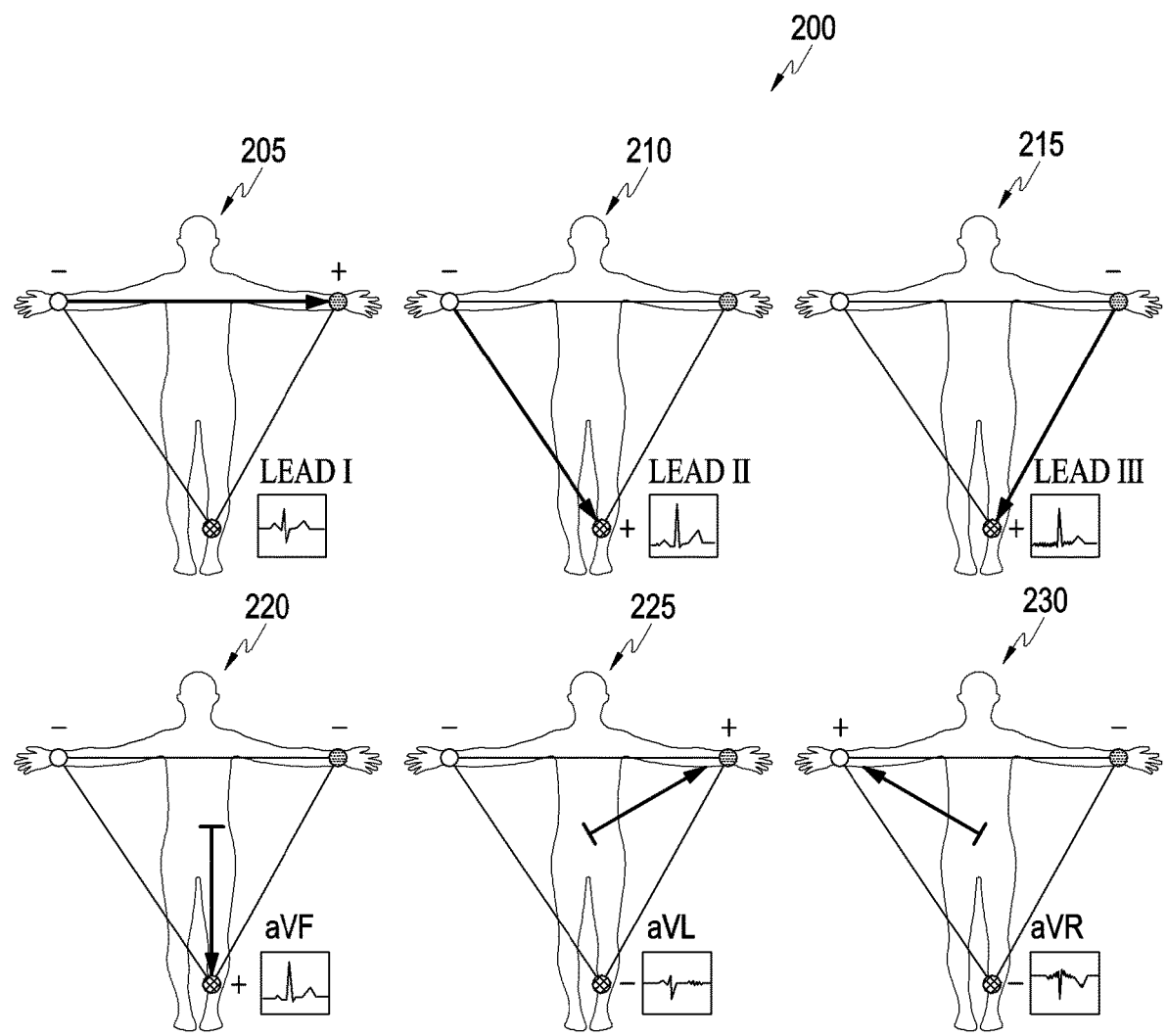
FIG. 2 is a view illustrating signals obtained by electrodes arranged on a user's body according to an embodiment.

FIG. 2 is a view 200 illustrating signals obtained by electrodes arranged on a user's body according to an embodiment.

Referring to FIG. 2, an electronic device for measuring the ECG may typically include four electrodes attached to both arms and both legs to obtain a record for a first lead (Lead I) 205, a second lead (Lead II) 210, a third lead (Lead III) 215, an argument voltage foot (aVF) 220, an argument voltage left (aVL) 225, and an argument voltage right (aVR) 230 and six electrodes attached to the chest to obtain a record for leads V1 to V6.

Lead refers to a voltage difference between two electrodes being shown as an ECG signal and may be divided into the first lead (Lead I) 205, the second lead (Lead II) 210, and the third lead (Lead III) 215 depending on measurement positions and the shape of the ECG signal may differ.

As shown in FIG. 2, the first lead 205 is a signal obtained in the right-to-left direction or left-to-right direction with respect to the heart, the second lead 210 is a signal obtained in the direction from the top right end of the chest to the left side of the lower abdomen, and the third lead 215 is a signal obtained in the direction from the top left end of the chest to the left side of the upper abdomen.

For example, a wearable electronic device of a wrist-worn type (e.g., a band or watch) may perform measurement while being attached on the user's wrist, thus obtaining the first lead of ECG signal. However, another lead of ECG signal other than the first lead may be obtained so as to obtain an accurate ECG measurement result, as this may increase accuracy in continuous ECG monitoring. To that end, according to an embodiment, a wearable electronic device may be configured to be detachable from an external accessory, including an attaching pad. Thus, the wearable electronic device may obtain electrode signals via connection electrodes with the external accessory upon coupling with the external accessory. According to an embodiment, when the external accessory includes a communicable detachable measurement module, as well as the attaching pad, the wearable electronic device may detachably coupled with the detachable measurement module. While coupled with the detachable measurement module, the wearable electronic device may obtain electrode signals via a connection terminal(s) with the detachable measurement module. The wearable electronic device may establish communication with the external accessory. Thus, the wearable electronic device may transfer a control signal for obtaining electrode signals according to a combination of electrodes via communication connections with the detachable measurement module, and may obtain electrode signals according to the combination of electrodes via the connection terminals of the detachable measurement module, in response to the control signal.

The external accessory may couple with the wearable electronic device directly, or via the detachable measurement module included in the external accessory. The external accessory may provide electrode signals to the wearable electronic device and may also be referred to as an external device, external electronic device, or biometric signal measurement device.

Figure 3:
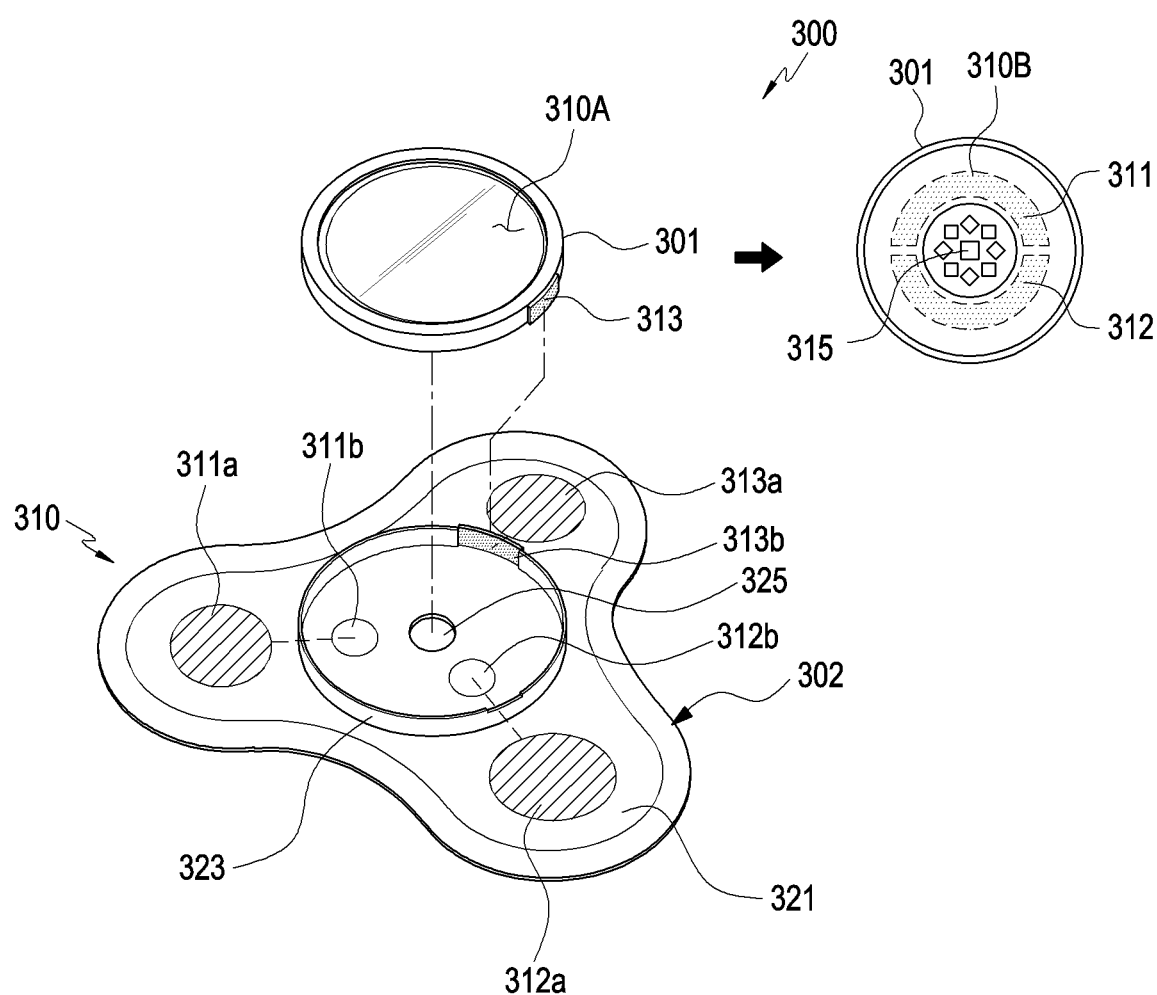
FIG. 3 is an exploded perspective view illustrating a detachable wearable electronic device and an external accessory including an attaching pad according to an embodiment.

FIG. 3 is an exploded perspective view 300 illustrating a detachable wearable electronic device and an external accessory including an attaching pad according to an embodiment.

Referring to FIG. 3, a wearable electronic device 301 (e.g., the electronic device 101 of FIG. 1A) may be implemented to be detachable from an external accessory 310. The wearable electronic device 301 may have a side bezel structure to allow the wearable electronic device 301 to be coupled with the external accessory 310 after it decouples from the coupling members (e.g., the coupling members 150a and 160a of FIG. 1B).

According to an embodiment, the external accessory 310 may include an attaching pad 302. According to an embodiment, the attaching pad 302 may attach the wearable electronic device 301 to the user's body. According to an embodiment, the attaching pad 302 may be a limited use item, in light of adhesion issues and/or sanitary issues such as contamination and infection. In some embodiments, it may be a single-use item according to clinical recommendations.

According to an embodiment, the wearable electronic device 301 may couple with the external accessory 310 by a coupling structure or via, for example, a magnetic force. According to an embodiment, the wearable electronic device 301 may receive input of a selection via a user interface displayed on the screen of the wearable electronic device 301 when coupling with the wearable electronic device 301, so that a coupling with the external accessory 310 may be detected when it couples with the external accessory 310. According to an embodiment, the electrodes included in the wearable electronic device 301 may be electrically connected with the connection terminals of the external accessory 310, and coupling may be detected via detection of a signal by the connected terminal. A configuration for detecting a coupling between the wearable electronic device 301 and the external accessory 310 may not be limited thereto. When the attaching pad 302 is discarded and replaced with another attaching pad 302 upon expiry of limited uses, the wearable electronic device 301 may couple with the external accessory 310 using a new attaching pad.

According to an embodiment, the attaching pad 302 may include a pad body 321 typically formed of a flexible sheet and a coupling member 323 provided on one surface of the pad body 321. The coupling member 323 may be provided to surround a portion of the wearable electronic device 301, such as the bottom surface of the wearable electronic device 301. For example, the coupling member 323 may have a circular fence shape protruding from one surface of the pad body 321, thereby providing a predetermined degree of fastening force, while providing guidance for coupling with the wearable electronic device 301.

According to an embodiment, the wearable electronic device 301 may include an aligning key structure, which may set a direction in which the wearable electronic device 301 couples to the attaching pad 302. For example, when aligned along a predetermined direction from the attaching pad 302, the wearable electronic device 301 may stably couple with the attaching pad 302, e.g., the coupling member 323. According to an embodiment, the aligning key structure may include a combination of a first aligning key protruding from the bottom surface of the wearable electronic device 301, and a second aligning key formed in the shape including a depression in the coupling member 323. This aligning key structure may be designed in various shapes and positions and may guide the wearable electronic device 301 to couple with the external accessory in the designated direction.

According to an embodiment, an adhesive may be applied to an opposite surface of the pad body 321, e.g., the surface opposite to the surface where the coupling member 323 is disposed. For example, the opposite surface of the pad body 321, e.g., the bottom surface of the pad body 321, which is hidden in FIG. 3, may be attached to the user's body. When attached to the user's body, the pad body 321 may be formed of a flexible sheet, and be formed in various shapes suitable to a body curvature. For example, the pad body 321 may be formed of a material or in a shape which allows the pad body 321 to be easily attached to the user's body. According to an embodiment, the region where the wearable electronic device 301 couples with the pad body 321, e.g., the coupling member 323, may have a predetermined degree of stiffness. For example, the pad body 321 may be flexibly transformed to fit the body curve while maintaining the state of coupling with the wearable electronic device 301.

According to an embodiment, in a plane view, the wearable electronic device 301, or at least the bottom surface of the wearable electronic device 301, may include a circular shape, but without limitations thereto, it may have other various shapes, e.g., a polygon. The shape of the wearable electronic device 301 may facilitate disposition of more electrodes (e.g., electrodes for biometric signal detection or electrical signal transfer) in a limited area (e.g., the area of the bottom surface of the wearable electronic device 301). When detecting a biometric signal, if the area of contact between electrode and the body is increased, the accuracy of measurement increases. For example, when at least two of the plurality of electrodes contact the user's body, a biometric signal may be detected via the corresponding electrodes. According to an embodiment, when a plurality of electrodes contacts the user's body, two electrodes from among the plurality may be arbitrarily selected as lead electrodes. For example, when three electrodes are used for biometric signal measurement, three electrode combination pairs (e.g., a first lead, a second lead, and a third lead) may be possible and, as a biometric signal is detected via each electrode combination, the detected biometric information may be diversified or the accuracy of the detected biometric information may be enhanced.

According to an embodiment, the electrodes arranged in the wearable electronic device 301 may provide a path for transferring the voltage or current signal corresponding to the substantially detected biometric signal, and the measurement electrode(s) 311a, 312a, and 313a contacting the user's body may be provided in the attaching pad (e.g., the opposite surface of the pad body 321). For example, the measurement electrodes 311a, 312a, and 313a may be electrically connected with the wearable electronic device 301 via wires provided inside the coupling member 323 or the pad body 321. Since the pad body 321 may be flexibly transformed corresponding to the body curve, it may provide an environment in which a sufficient interval may be secured between the measurement electrodes 311a, 312a, and 313a.

More details regarding the arrangement of the measurement electrodes and the structure of electrical connection to the wearable electronic device 301, the front surface 310A and rear surface 310B of the wearable electronic device 301 are provided below. Referring to FIG. 3, a first electrode 311 for measuring biometric signals may be disposed on the rear surface 310B of the wearable electronic device 301, and a second electrode 312 for applying voltage to the first electrode 311 and a third electrode 313 (e.g., the key input devices 103a and 104a of FIG. 1B) may be disposed on the same surface as the first electrode 311. The third electrode 313 for measuring biometric signals may be disposed on a side surface of the wearable electronic device 301 which may be contacted by the other hand of the user than the hand holding the wearable electronic device 301. According to an embodiment, the third electrode 313 may be disposed to protrude from a side surface of the wearable electronic device 301. When the wearable electronic device 301 couples with the coupling member 323, the third electrode 313 may contact the connection terminal 313b of the coupling member 323 and electrically connect via the connection terminal 313b. For example, the third electrode 313 may be placed on the right side surface of the wearable electronic device 301 to allow the user to touch with his finger, and the third electrode 313 may be disposed to be mapped to the key input devices 103a and 104a of FIG. 1B. According to an embodiment, the third electrode 313 may be included, as a transparent electrode, in the display (e.g., the display 120a of FIGS. 1B and 1D) of the wearable electronic device 301 and be touched by a second portion (e.g., finger) of the user's body. According to an embodiment, the third electrode 313 may be disposed in the bezel (e.g., 106a of FIG. 1B) of the wearable electronic device 301 and be touched by the second portion (e.g., finger) of the user's body. According to an embodiment, when the wearable electronic device 301 is bezel-less, the third electrode 313 may be disposed on the housing (e.g., the housing 110a of FIG. 1B) of the wearable electronic device 301 and be touched by the second portion (e.g., finger) of the user's body.

As described above, the third electrode 313 which may be touched by the second portion (e.g., finger) of the user's body, with the wearable electronic device 301 worn on the user's wrist and the first portion (e.g., wrist) of the user's body contacting the first electrode 311 and the second electrode 312, may be disposed in various positions. Thus, the coupling structure between the connection terminal 313b and the third electrode 313 may be designed to have various shapes and positions.

Although FIG. 3 illustrates an example in which the second electrode 312 is disposed on the same surface (e.g., the rear surface) as the first electrode 311, and the third electrode 313 is disposed on a side surface of the wearable electronic device 301, the arrangement is not limited thereto. For example, one side surface between the front and rear surface of the wearable electronic device 301, e.g., a portion (e.g., edge) of the housing of the wearable electronic device 301 or the entire edge of the housing may be formed of the same material (e.g., metal), and any one of the portion of the edge or the entire edge formed of the same material may be used as the third electrode 313. A photoplethysmography (PPG) sensor 315 for heartrate measurement may be mounted on the rear surface 310B of the wearable electronic device 301.

According to an embodiment, an opening 325 may be formed in the position corresponding to the PPG sensor 315 mounted on the rear surface of the wearable electronic device 301 in the space receiving the wearable electronic device 301. The opening 325 may be denoted a hole and may have a structure in which it is divided by a barrier depending on the position of at least one light receiving unit and at least one light emitting unit of the PPG sensor 315 of the wearable electronic device 301, and such barrier structure may be used as a path for measuring the PPG signal. Such structure is described below with reference to FIG. 12.

According to an embodiment, when the wearable electronic device 301 couples with the coupling member 323 of the external accessory 310, the first electrode to third electrode 311, 312, and 313 of the wearable electronic device 301 may be electrically connected with the electrodes 311a, 312a, and 313a included in the attaching pad 302 via wires or connection terminals 311b, 312b, and 313b provided inside the coupling member 323 or the pad body 321. According to an embodiment, a wire or connection terminal 313b may be formed in a predetermined portion of the inner surface of the coupling member 323 to be electrically connected with the third electrode 313 of the wearable electronic device 301 when the wearable electronic device 301 is coupled with the external accessory 310.

According to an embodiment, connection between the measurement electrodes 311a, 312a, and 313a and the first electrode to third electrode 311, 312, and 313 of the wearable electronic device 301 may be controlled via switching. For example, a combination of at least two of the measurement electrodes 311a, 312a, and 313a may be connected with a combination of at least two of the first electrode to third electrode 311, 312, and 313 to obtain a biometric signal of first lead Lead I, second lead Lead II, or third lead Lead III. The electrical connection structure between the measurement electrodes 311a, 312a, and 313a and the first electrode to third electrode 311, 312, and 313 of the wearable electronic device 301, e.g., a connection structure via a MUX, is described below.

Figure 4A:
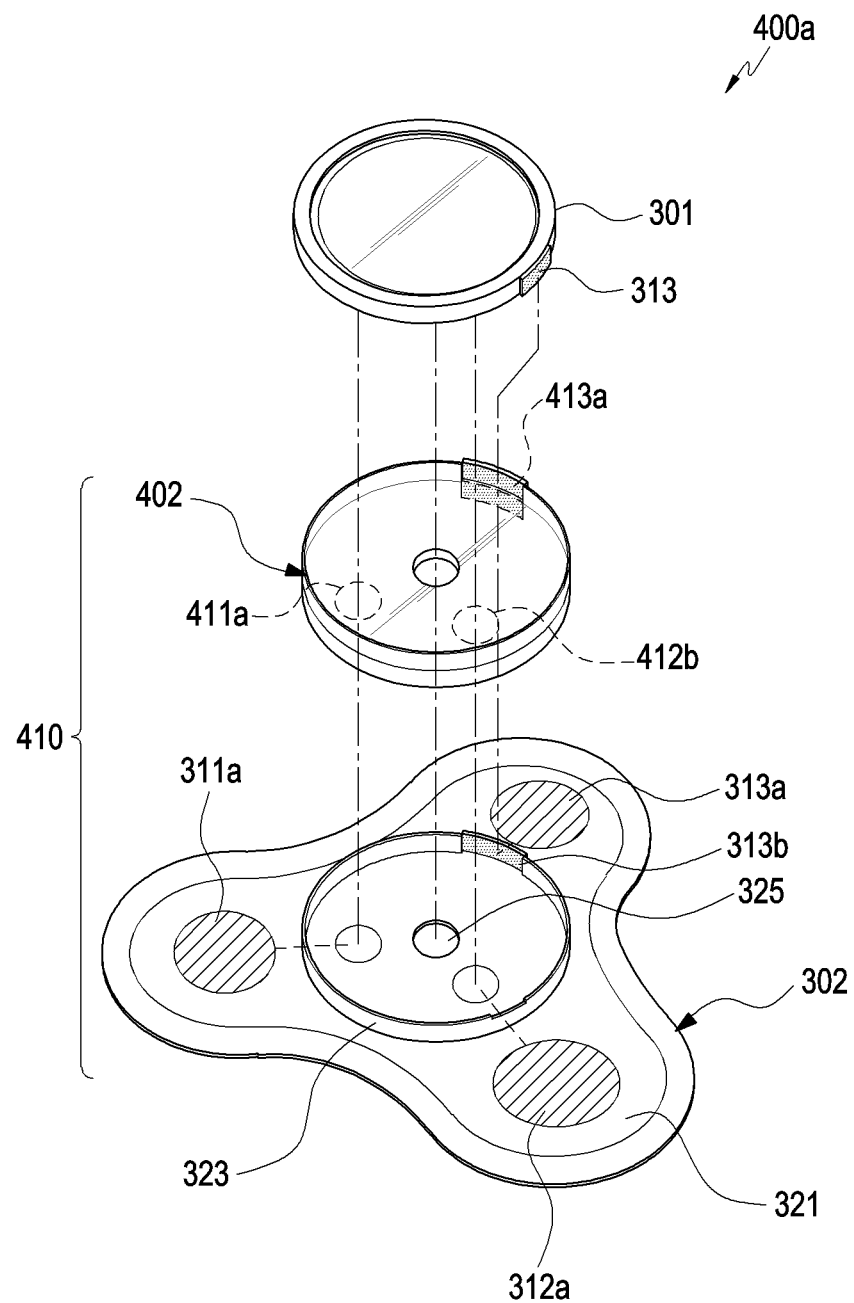
FIG. 4A is a perspective view illustrating a wearable electronic device coupled with an external accessory including an attaching pad and a detachable measurement module according to an embodiment.
Figure 4B:
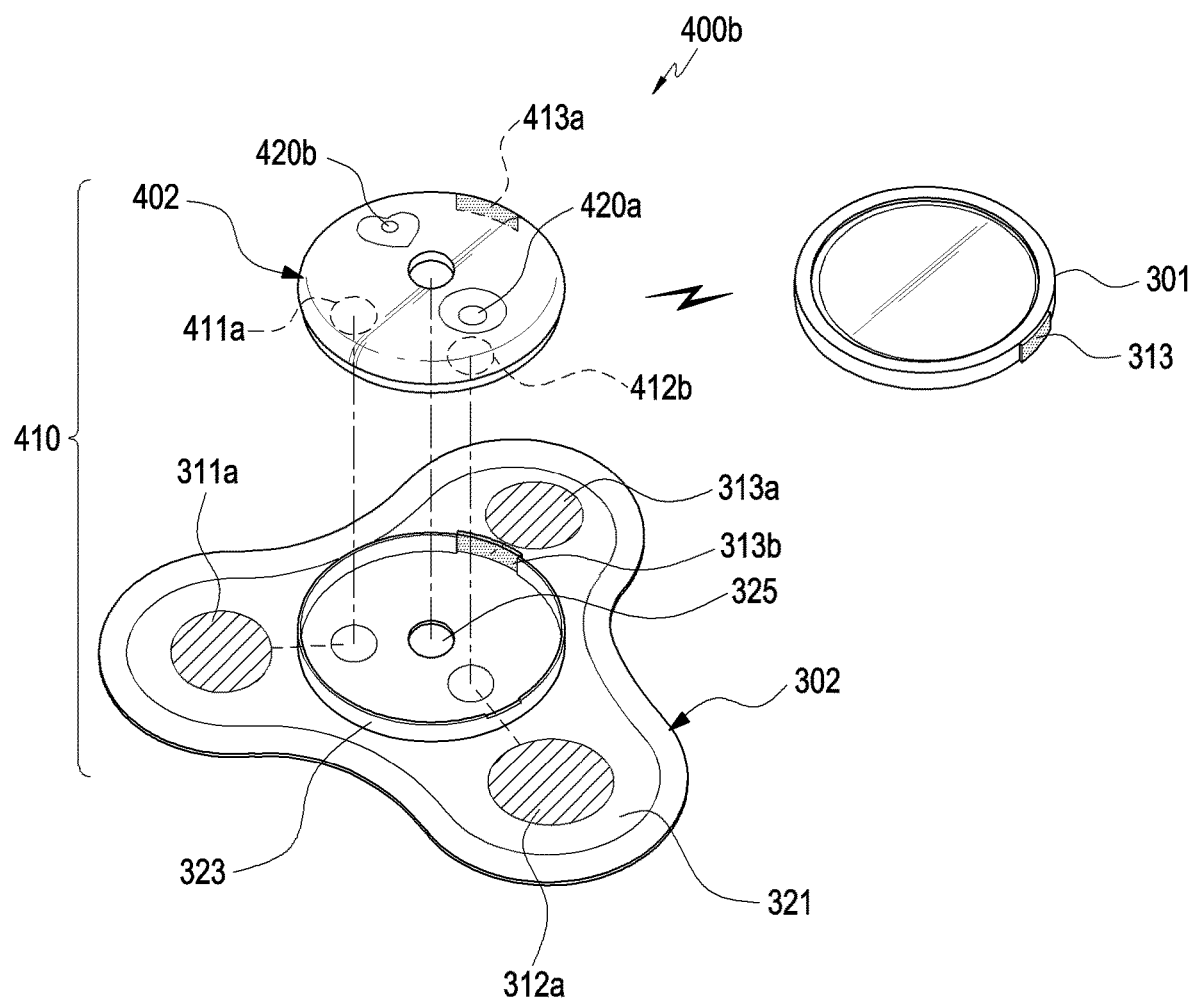
FIG. 4B is an exploded perspective view illustrating an external accessory including an attaching pad and a detachable measurement module according to an embodiment.
Figure 4C:
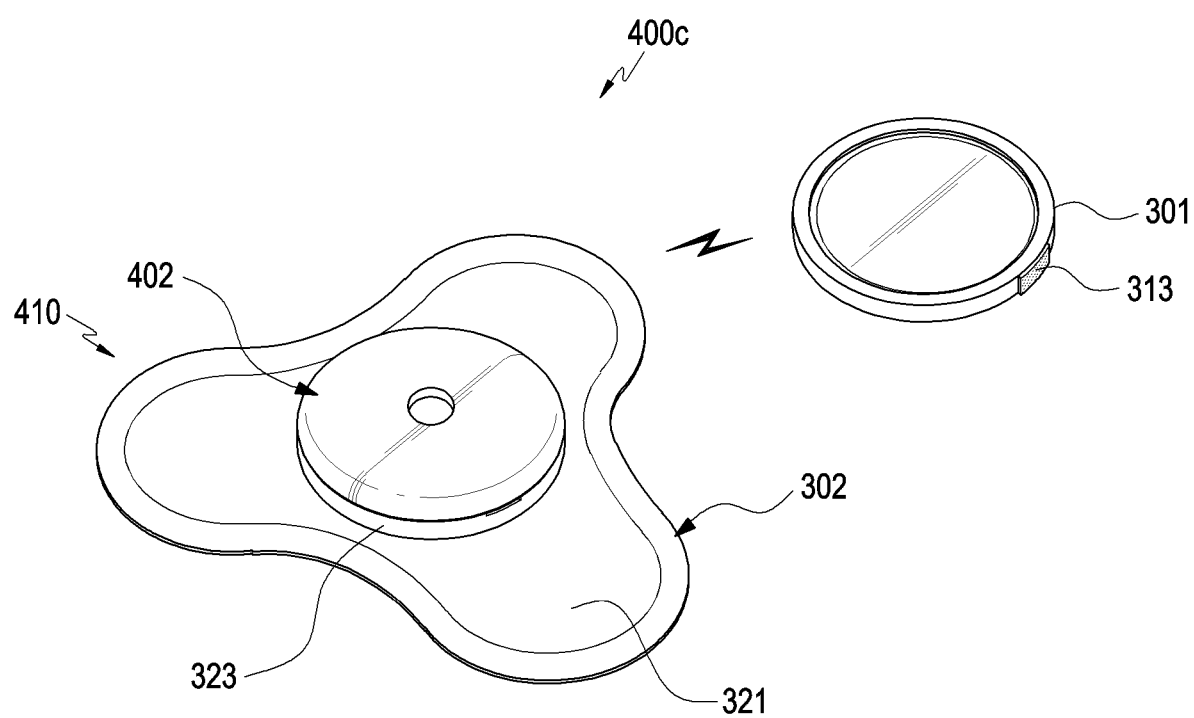
FIG. 4C is a perspective view illustrating an assembled external accessory including an attaching pad and a detachable measurement module according to an embodiment.

FIG. 4A is a perspective view 400a illustrating a wearable electronic device coupled with an external accessory, including an attaching pad and a detachable measurement module according to an embodiment. FIG. 4B is an exploded perspective view 400b illustrating an external accessory including an attaching pad and a detachable measurement module according to an embodiment. FIG. 4C is a perspective view 400c illustrating an assembled external accessory including an attaching pad and a detachable measurement module according to an embodiment.

Referring to FIGS. 4A to 4C, an external accessory 410 may include a detachable housing (e.g., a detachable measurement module 402) and an attaching pad 302.

According to an embodiment, the wearable electronic device 301 may indicate/notify a detected coupling to the external accessory 410 in various manners. According to an embodiment, upon coupling with the external accessory 410, a coupling notification may be displayed on the screen of the wearable electronic device 301, and content providing guidance for the mounting direction may be displayed. Thus, the user may be notified as to whether electrodes are properly connected via the screen. According to an embodiment, signal detection in the wearable electronic device 301 via the electrodes of the external accessory 410 may indicate that the external accessory 410 is stably attached to the user's body and is electrically connected thereto, and is coupled with the external accessory 410. Alternatively, the wearable electronic device 301 may be led to be mounted on the external accessory 410 in a hardware type, via, e.g., hooks, coupling structure, groove, or hall sensor. As such, whether the wearable electronic device 301 is normally coupled with the external accessory 410 may be identified by a hardware or software method, and the methods are not limited thereto.

According to an embodiment, the bottom surface (or bottom face) of the detachable measurement module 402, e.g., the surface facing the attaching pad 302, may be a flat surface, and the top surface may be formed in a shape to be coupled with the wearable electronic device 301. For example, as shown in FIG. 4A, the top surface of the detachable measurement module 402 may be shaped to surround the bottom surface of the wearable electronic device 301. The top surface of the detachable measurement module 402 may be formed to have a fence shape to surround the bottom surface of the wearable electronic device 301 like in the coupling member 323 of the attaching pad 302 in the form of allowing the wearable electronic device 301 to be fitted thereto.

Alternatively, the top surface of the detachable measurement module 402 may be a flat surface or may be formed in a dome shape as shown in FIGS. 4B and 4C. For example, the detachable measurement module 402 may have an internal space to receive such components as a processor or communication circuit. As such, the top surface of the detachable measurement module 402 may be formed in various shapes considering other band types than the wearable electronic device 301. According to an embodiment, as shown in FIGS. 4B and 4C, the detachable measurement module 402 may include a manipulation unit 420a for manipulating the switching device of the power unit and an output unit 420b for outputting light, images, or sound to the outside. The manipulation unit 420a and the output unit 420b may be placed on the top surface of the detachable measurement module 402, so that the detachable measurement module 402 may be exposed to the outside even when coupled with the attaching pad 302.

According to an embodiment, the detachable measurement module 402 may include connection terminals 411a, 412b, and 413a that may be electrically connected with the electrodes 311a, 312a, and 313a included in the attaching pad 302 when the detachable measurement module 402 is coupled to the coupling member 323 of the external accessory 310. For example, the detachable measurement module 402 may include a connection terminal 413a in the position corresponding to the connection terminal 313b provided inside the coupling member 323 and may further include connection terminals 411a and 412b in the positions corresponding to the wires or connection terminals 311b and 312b provided inside the coupling member 323 or the pad body 321. The connection terminals 411a, 412b, and 413a of the detachable measurement module 402 may electrically contact or connect to the electrodes (e.g., the first electrode 311, second electrode 312, and third electrode 313 of FIG. 3), respectively, disposed to be exposed to the outside of the wearable electronic device 301. A coupling between the wearable electronic device 301 and the detachable measurement module 402 may be identified via the connection terminals 414a, 412b, and 413a which may be respectively connected or contacted electrically.

According to an embodiment, the detachable measurement module 402 may play a role to transfer the voltage or current signal corresponding to the biometric signal substantially detected from the measurement electrode(s) 311a, 312a, and 313a contacting the user's body included in the attaching pad 302 to the wearable electronic device 301. According to an embodiment, the detachable measurement module 402 may select at least two electrodes as a lead, when the plurality of electrodes 311a, 312a, and 313a contact the user's body. Such combinations of the measurement electrodes may be sequentially selected and may transmit the signal detected using the measurement electrodes to the wearable electronic device 301 via the communication circuit of the detachable measurement module 402.

According to an embodiment, the detachable measurement module 402 may be operated by the internal battery or may receive power from the wearable electronic device 301 and operate.

Figure 5:
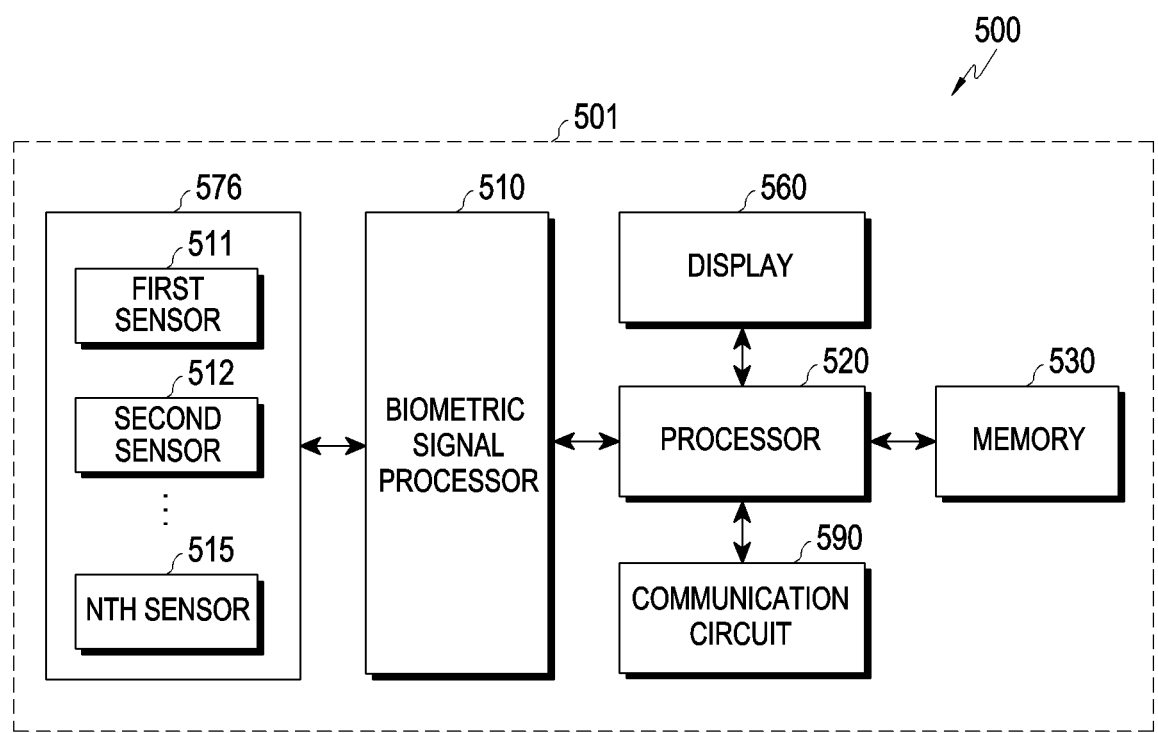
FIG. 5 is a block diagram illustrating an internal configuration of a wearable electronic device according to an embodiment.

FIG. 5 is a block diagram 500 schematically illustrating a wearable electronic device according to an embodiment.

Referring to FIG. 5, a wearable electronic device 501 may include a sensor module 576, a biometric signal processor 510, a processor 520, a memory 530, a display 560, and a communication circuit 590.

According to an embodiment, the sensor module 576 may include a plurality of sensors 511 to 515. The biometric signal processor 510 may perform processing to obtain different biometric signals from the plurality of sensors 511 to 515. According to an embodiment, examples of measurable biometric signals may include electrical signals, such as electrocardiogram (ECG), electroencephalography (EEG), and electromyography (EMG), physical signals, such as blood pressure, body temperature, and PPG, and/or composition-related signals, such as blood glucose level, oxygen saturation, and body composition. However, the measurable biometric signals are not limited thereto.

According to an embodiment, the plurality of sensors may include biometric sensors, such as an electrocardiogram sensor (hereinafter, ECG sensor), a photoplethysmography sensor (hereinafter, PPG sensor), a heart rate sensor, and a body temperature sensor and, may include optionally other various sensors for measuring biometric signals, such as an acceleration sensor but embodiments of the disclosure are not limited thereto.

According to an embodiment, when a plurality of sensors are used, upon measuring an ECG signal, the acceleration, PPG, and (SpO2; i.e., saturation of percutaneous oxygen) may be measured as well. The blood pressure may be measured using the ECG and PPG signals, and sleep apnea may be measured using the acceleration and SpO2 signal. For example, the measurement value from the acceleration sensor may measure the change in the height of the chest during breathing and the user's toss-and-turn. In particular, the SpO2 measurement value is a measurement of the blood oxygen concentration and sleep apnea may be detected by determining whether the SpO2 measurement value reduces.

Besides those described above, the processor 520 may generate measurement information regarding the temperature or humidity or the user's amount of exercise detected using various sensors and store the measurement information in the memory 530 and may be used to detect the user's amount of exercise or the environment when the biometric signal is measured. The measurement information obtained using various sensors may be utilized as basic data for analyzing the user's fitness or health condition. Various symptoms, such as blood pressure and sleep apnea, as well as simple heart checkup, may be measured by using various sensors together, thereby providing a complex health-care function.

According to an embodiment, when a first sensor 511 is an ECG sensor, the first sensor 511 may include a plurality of electrodes for ECG measurement. The biometric signal processor 510 may perform processing for obtaining a biometric signal based on the signals transferred via the plurality of electrodes. According to an embodiment, the biometric signal processor 510 may perform various signal processing, such as differential amplification, filtering, and analog-to-digital (AD) conversion and, to that end, may include a differential amplifier, a filtering unit, and an AD converter.

According to an embodiment, when the wearable electronic device 501 couples with an external accessory (e.g., the external accessory 310 of FIG. 3), a plurality of electrodes (e.g., the first electrode 31,1 the second electrode 312, and the third electrode 313 of FIG. 3) for ECG measurement of the wearable electronic device 501 may electrically contact or connect to the measurement electrodes 311a, 312a, and 313a included in the attaching pad of the external accessory, via connectable wires or terminals. Thus, signals transferred via the plurality of electrodes of the first sensor 511 may be signals transferred via connection with the measurement electrodes of the attaching pad.

According to an embodiment, when the wearable electronic device 501 establishes communication with an external accessory (e.g., the external accessory 410 of FIG. 4A), the wearable electronic device 501 may receive the signals measured using the measurement electrodes 311a, 312a, and 313a included in the attaching pad of the external accessory, via the communication circuit 590.

According to an embodiment, when the second sensor 512 is an optical sensor, e.g., a PPG sensor, the second sensor 512 may include at least one light receiving unit and at least one light emitting unit. The at least one light emitting unit may include a plurality of light emitting diodes (LEDs). The at least one light receiving unit may include an optical sensor and may receive the light reflected by at least one of the user's blood vessel and skin among the light beams output from the at least one light emitting unit. The at least one light receiving unit may be a photo diode. The second sensor 512 may generate at least one piece of biometric information using the electrical signal into which the light has been converted and the biometric information may be a PPG signal. The biometric signal processor 510 may receive a current corresponding to the measured PPG signal from the second sensor 512 and convert the measured PPG signal into a digital signal and transfer the digital signal to the processor 520. According to an embodiment, the biometric signal processor 510 may perform current-to-voltage conversion, amplification, filtering, and AD conversion for processing the PPG signal.

According to an embodiment, the biometric signal processor 510 may include an analog front end (AFE) for processing the signals output from the plurality of sensors 511 to 515. For example, the AFE of the biometric signal processor 510 may convert the analog voltage signals output from the plurality of sensors 511 to 515 into digital signals and transfer the digital signals to the processor 520.

According to an embodiment, the processor 520 may detect, predict, or analyze the user's ECG state based on the biometric signal from the biometric signal processor 510. According to an embodiment, the processor 520 may obtain a biometric signal based on the difference between the voltages measured at, at least, two electrodes among the plurality of electrodes from the biometric signal processor 510 and analyze the biometric signal. For example, the processor 520 may detect, predict, or analyze cardiac arrhythmias such as ventricular fibrillation and ventricular tachycardia using the ECG signal. As such, the processor 520 may analyze the signals measured using the plurality of sensors 511 to 515 and provide at least one piece of biometric information. The at least one piece of biometric information may be information such as heart rate, cardiac arrhythmia, blood pressure, and sleep apnea. According to an embodiment, the processor 520 may display the at least one piece of biometric information using the display 560. For example, when the biometric signal meets a predetermined condition (e.g., a predetermined range or more or less), the processor 520 may provide a notification (e.g., a warning).

According to an embodiment, the memory 530 may store data (e.g., biometric information) from the wearable electronic device 501. The memory 530 may be implemented in substantially the same or similar manner to the memory 130 described above in connection with FIG. 1A. The memory 530 may be implemented as a non-volatile memory.

According to an embodiment, the display 560 may be implemented in substantially the same or similar manner to the display device 160 described above in connection with FIG. 1A. According to an embodiment, the display 560 may receive at least one piece of biometric information from the processor 520 and visually display the same. For example, the display 560 may display the at least one piece of biometric information in a time domain graph or frequency domain graph.

According to an embodiment, the communication circuit 590 may be implemented in substantially the same or similar manner to the communication module 190 described above in connection with FIG. 1A. According to an embodiment, the processor 520 may discover a peripheral external accessory (e.g., the external accessory 410 of FIG. 4A) using the communication circuit 590 and establish communication with the external accessory. According to an embodiment, the processor 520 may transfer a control signal for controlling the external accessory via the communication circuit 590. According to an embodiment, the external accessory may stay attached to the user's body and may control the external accessory using the communication circuit 590 to measure the user's biometric information. Thus, the communication circuit 590 may receive the measured biometric information from the external accessory.

According to an embodiment, a wearable electronic device (e.g., 301 of FIGS. 3 to 4C or 501 of FIG. 5) includes at least one sensor 576 including a plurality of electrodes (e.g., the first electrode 311, the second electrode 312, and the third electrode 313 of FIG. 3), at least one processor 520 operatively connected with the at least one sensor, and a memory 530 operatively connected with the at least one processor 520. The memory 530 may store instructions executed to enable the at least one processor 520 to, upon detecting a coupling with an external accessory (e.g., 310 of FIG. 3 or 410 of FIGS. 4A to 4C) contacting a user's body, measure a biometric signal based on a voltage received via at least two of a plurality of measurement electrodes (e.g., the measurement electrodes 311a, 312a, and 313a of FIG. 3) included in the external accessory.

According to an embodiment, the external accessory may include an attaching pad (e.g., 302 of FIG. 3) including the plurality of measurement electrodes detachably provided on one surface of a housing of the wearable electronic device.

According to an embodiment, the instructions may be configured to enable the at least one processor to detect the coupling with the external accessory as the plurality of electrodes arranged to be exposed to an outside of the wearable electronic device respectively electrically contact or connect to the plurality of measurement electrodes of the attaching pad respectively via a connectable first connection terminal (e.g., 311b, 312b, and 313b of FIG. 3).

According to an embodiment, the instructions may be configured to enable the at least one processor to sequentially control switching for connecting at least two electrodes among the plurality of electrodes included in the at least one sensor with at least two measurement electrodes among the plurality of measurement electrodes of the external accessory.

According to an embodiment, the instructions may be configured to enable the at least one processor to, when any one of the plurality of electrodes included in the at least one sensor is a reference electrode, sequentially control switching for connecting at least two electrodes, except for the reference electrode among the plurality of electrodes, with at least two measurement electrodes among the plurality of measurement electrodes of the external accessory.

According to an embodiment, the instructions may be configured to enable the at least one processor to measure the biometric signal based on the received voltage as at least two of the plurality of electrodes included in the at least one sensor connect to at least two of the plurality of measurement electrodes of the attaching pad via the first connection terminal, in response to the switching.

According to an embodiment, the instructions may be configured to enable the at least one processor to, when a detachable measurement module (e.g., 402 of FIG. 4A) including a communication circuit is coupled to the external accessory, transmit a signal for sequentially controlling the switching to the detachable measurement module via communication with the detachable measurement module.

According to an embodiment, the detachable measurement module may include a second connection terminal (e.g., 411a, 411b, and 413a of FIG. 4A) to allow the plurality of measurement electrodes included in the attaching pad to electrically contact or connect with, respectively, the plurality of electrodes of the wearable electronic device. The detachable measurement module may include a coupling structure to which the wearable electronic device can be coupled.

According to an embodiment, the instructions may be configured to enable the at least one processor to, upon detecting the coupling with the external accessory, enter a measurement mode for measuring the biometric signal.

According to an embodiment, the instructions may be configured to enable the at least one processor to, upon entering the measurement mode, deactivate remaining functions except for a function related to measurement of the biometric signal.

According to an embodiment, the instructions may be configured to enable the at least one processor to, when the at least one sensor includes an optical sensor, measure an additional biometric signal for the user using at least one light receiving unit and at least one light emitting unit included in the optical sensor and measure a blood pressure using the measured additional biometric signal.

Figure 6:
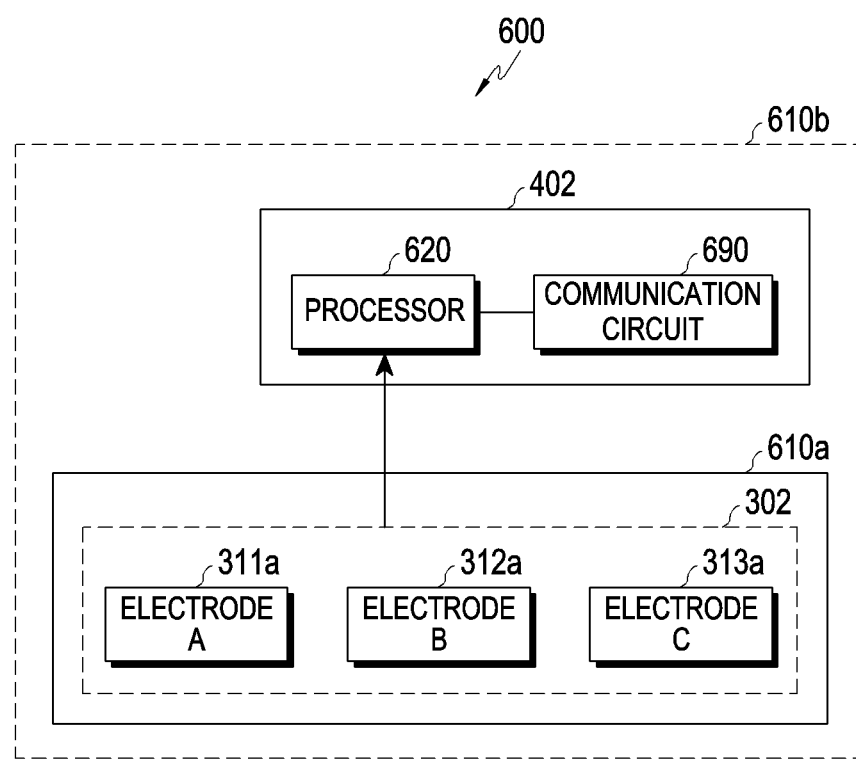
FIG. 6 is a block diagram illustrating an internal configuration of an external accessory according to an embodiment.

FIG. 6 is a block diagram 600 illustrating an internal configuration of an external accessory according to an embodiment.

According to an embodiment, an external accessory may denote both one including an attaching pad alone and another including a combination of an attaching pad and a detachable measurement module.

According to an embodiment, when the wearable electronic device (e.g., the wearable electronic device 301 of FIG. 3) is implemented to couple with the external accessory (e.g., the external accessory 310 of FIG. 3), the external accessory 610a may be configured to include the attaching pad 302 alone, which is detachably provided on one surface of the housing of the wearable electronic device, as shown in FIG. 6. The attaching pad 302 may attach to the user's or patient's body and may include electrodes (e.g., electrodes A to C) 311a, 312a, and 313a which directly contact the user's body. The electrodes (e.g., electrodes A to C) 311a, 312a, and 313a may be electrically connected with the electrodes of the wearable electronic device via contacts (e.g., the connection terminals 311b, 312b, and 313b of FIG. 3) within the coupling member (e.g., the coupling member 323 of FIG. 3) of the attaching pad 302.

When the wearable electronic device (e.g., the wearable electronic device 301 of FIG. 4A) is implemented to communicate with the external accessory (e.g., the external accessory 410 of FIG. 4A), the external accessory 610b may further include a detachable measurement module 402 coupled to the attaching pad 302 as shown in FIG. 6.

According to an embodiment, the detachable measurement module 402 may include a processor 620 and a communication circuit 690. The processor 620 and the communication circuit 690 may be embedded in a single housing (e.g., the detachable measurement module 402 of FIG. 4A) and, according to an embodiment, may further include a multiplexer (MUX), a display, and a switching device (e.g., the manipulation unit 420a of FIG. 4A) for powering on/off or for starting/ending measurement. According to an embodiment, the processor 620 may include an analog front end (AFE). Alternatively, the AFE may be included in the wearable electronic device (e.g., the biometric signal processor 510 or processor 520 of FIG. 5), not in the processor 620 of the detachable measurement module 402. For example, when the processor 620 includes an AFE, the signals, e.g., analog voltage signals, detected via the measurement electrodes may be converted into digital signals that may then be transmitted to the wearable electronic device via the communication circuit 690. Alternatively, when the processor 620 includes no AFE, the signals detected via the measurement electrodes may be, without conversion, transmitted to the wearable electronic device via the communication circuit 690.

According to an embodiment, the information generated by the processor 620 may be transmitted to another electronic device (e.g., the electronic device 104 of FIG. 1A) or a server (e.g., the server 108 of FIG. 1A) via the communication circuit 690 and a network (e.g., the second network 199 of FIG. 1A).

According to an embodiment, with the detachable measurement module 402 coupled to the attaching pad 302, the external accessory 610b may wirelessly connect to the wearable electronic device (e.g., the wearable electronic device 301 of FIG. 4A) using the communication circuit 690. For example, the communication circuit 690 may support communication between the wearable electronic device and the external accessory. According to an embodiment, the communication circuit 690 may receive, from the wearable electronic device, a signal for controlling an electrode combination of at least two electrodes among the plurality of electrodes A to C (311a, 312a, and 313a) in a communication scheme, e.g., Bluetooth, Wi-Fi, or near-field communication (NFC). According to an embodiment, while staying coupled with the external accessory 610b, the wearable electronic device receives signals via the electrodes physically connected with the external accessory 610b. Thus, the wearable electronic device may transmit signals for controlling the electrodes to the external accessory 610b via the communication circuit 690.

For example, when biometric signal measurement starts, control signals for controlling switching at each predetermined time may be received from the wearable electronic device via the communication circuit 690 of the detachable measurement module 402. In response to the control signal, at least two of the plurality of electrodes A to C (311a, 312a, and 313a) may be electrically connected with at least two of the electrodes (e.g., the first electrode 311, the second electrode 312, and the third electrode 313 of FIG. 3) of the wearable electronic device.

Figure 7:
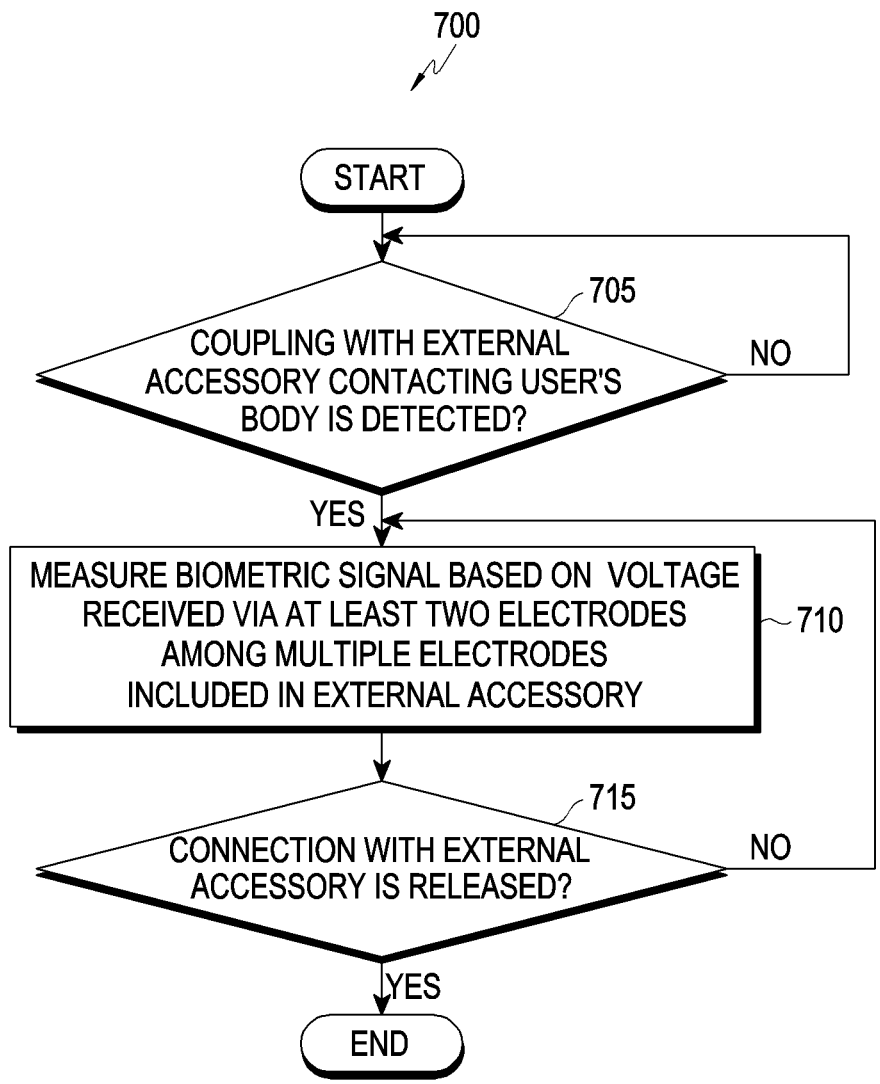
FIG. 7 is a flowchart illustrating operations of a wearable electronic device for processing a biometric signal according to an embodiment.

FIG. 7 is a flowchart 700 illustrating operations of a wearable electronic device for processing a biometric signal according to an embodiment.

Referring to FIG. 7, the operation method may include operations 705 to 715. Each step/operation of the operation method of FIG. 7 may be performed by at least one of a wearable electronic device (e.g., the electronic device 101 of FIG. 1A or the wearable electronic device 501 of FIG. 5), or at least one processor (e.g., the processor 120 of FIG. 1A and the processor 520 of FIG. 5) of the wearable electronic device. According to an embodiment, at least one of operations 705 to 715 may be omitted, some operations thereof may be performed in reverse order, and/or other operations may be added thereto.

According to an embodiment, in operation 705, the wearable electronic device may detect coupling with an external accessory that is contact with the user's body.

According to an embodiment, the wearable electronic device may be attached to the user's body while remaining mounted on the external accessory. Alternatively, when the external accessory is attached to the user's body, the wearable electronic device may be coupled with the external accessory. According to an embodiment, when the wearable electronic device detects a coupling (or mounting) to the external accessory, a detection signal indicating coupling may be determined to be an input and/or request to execute biometric detection, monitoring and/or measurement.

According to an embodiment, the coupling with the external accessory may be detected based on a signal generated as the wearable electronic device is coupled to the attaching pad of the external accessory. For example, the wearable electronic device may detect the coupling by changing some of the plurality of electrodes or the communication circuit of the external accessory for communication purposes and reading information. As another example, the connection may be detected by receiving a user selection via the user interface displayed on the screen of the wearable electronic device when coupled with the wearable electronic device, as well as the signal generated as it couples to the attaching pad via a magnetic force.

According to an embodiment, when the wearable electronic device couples to the detachable measurement module-combined external accessory, the coupling may be detected via communication with the external accessory. Configurations for detecting the coupling or connection of the wearable electronic device to the external accessory may not be limited to what has been described above. According to an embodiment, upon first receiving a signal input via the measurement electrodes (e.g., electrodes A, B, and C (311a, 312a, and 313a) of FIG. 6) included in the external accessory when the external accessory is attached to the user's or patient's body, the wearable electronic device may identify that the external accessory has stably been attached to the user's body and determine that such signal is an 'input or request regarding measurement.' As described above, the reception of signals via the measurement electrodes may be a signal indicating that it is in contact with the user's body, and such a signal may be received when the wearable electronic device couples to the external accessory. Thus, whether it attaches to the user's body may be identified based on the reception of signals via the measurement electrodes regardless of the order of coupling, such as when the wearable electronic device couples to the external accessory with the external accessory attached to the user's body and when it is attached to the user's body while staying coupled with the external accessory.

In operation 710, the wearable electronic device may measure a biometric signal based on the voltage received via at least two among the plurality of electrodes included in the external accessory. According to an embodiment, upon detecting coupling (and/or connection) with the external accessory, the wearable electronic device may automatically switch to an operational mode enabling measurement of biometric signals. The mode may be referred to hereinafter as a 'patch mode.' In the patch mode, functions and menus related to biometric measurement may be provided (e.g., to the exclusion of other functions and menus irrelevant to biometric measurements) and the wearable electronic device may even disable, deactivate and/or restrict other functions irrelevant to biometric measurement. For example, the wearable electronic device may disable display options, deactivate Bluetooth functionality, etc. as these are irrelevant to biometric measurements.

According to an embodiment, initiation and termination in measurement of the biometric signal may be controlled manually, according to user input received to the wearable electronic device, or an electronic device (e.g., a smartphone) interoperating with the wearable electronic device. Alternatively, biometric measurement may be automatically controlled (e.g., in terms of activation or deactivation) using a lead-based on/off function.

In operation 715, the wearable electronic device may detect whether the connection with the external accessory is released (e.g., disconnected). According to an embodiment, disconnection may be detected based on a signal generated as the coupling between the external accessory and the attaching pad is released (e.g., decoupling), or, alternatively, the disconnection may be detected when communication with the external accessory terminates. According to an embodiment, after the measurement is complete, and when the user removes the wearable electronic device from the external accessory, the connection between the wearable electronic device and the external accessory may be terminated, and the wearable electronic device may automatically switch from the patch mode to a normal smart-watch mode. For example, when the wearable electronic device is removed from the external accessory, the connection between the wearable electronic device and the external accessory via contacts, e.g., the connection line via the electrodes, are disconnected Detection of this disconnection may trigger automatic switching from the measurement mode (e.g., patch mode) to an original normal mode (e.g., watch mode). Here, the normal mode denotes a mode in which operations are performed on the smart watch, and may also be referred to as a 'watch mode.' For example, the watch mode may include functions such as displaying a watch screen, executing an application, and checking a notification. According to an embodiment, when the user selects a release of communication connection via the screen of the wearable electronic device after measurement is done, the communication connection may terminate, and the wearable electronic device may automatically switch to the watch mode.

Configurations for detecting the disconnection from the external accessory by the wearable electronic device may not be limited to what has been described above. Upon detecting the disconnection from the external accessory, the wearable electronic device may terminate the patch mode and then switch to the watch mode. For example, the wearable electronic device may activate the functions which have been turned off or restricted as being irrelevant to biometric measurement or, in contrast, may turn off or restrict the functions related to biometric measurement.

A method for processing a biometric signal in a wearable electronic device (e.g., 301 of FIGS. 3 to 4C or 501 of FIG. 5) may include detecting a coupling with an external accessory (e.g., 310 of FIG. 3 or 410 of FIGS. 4A to 4C) contacting a user's body and measuring a biometric signal based on a voltage received via at least two measurement electrodes among a plurality of measurement electrodes (e.g., the measurement electrodes 311*a*, 312*a*, and 313*a* of FIG. 3) included in the external accessory, in response to detection of the coupling.

According to an embodiment, detecting the coupling with the external accessory may include detecting the coupling by a coupling structure of an attaching pad (e.g., 302 of FIG. 3) of the external accessory detachably provided on one surface of a housing of the wearable electronic device.

According to an embodiment, detecting the coupling with the external accessory may include detecting the coupling with the external accessory as a plurality of electrodes arranged to be exposed to an outside of the wearable electronic device respectively electrically contact or connect to the plurality of measurement electrodes of the attaching pad via a connectable first connection terminal (e.g., 311*a*, 31*b*, and 313*b* of FIG. 3). According to an embodiment, measuring the biometric signal may include sequentially controlling, on a per-predetermined time basis, switching for connecting at least two electrodes among the plurality of electrodes of the wearable electronic device with at least two measurement electrodes among the plurality of measurement electrodes of the external accessory.

According to an embodiment, measuring the biometric signal may include, when any one of the plurality of electrodes of the wearable electronic device is a reference electrode, controlling switching for connecting at least two electrodes, except for the reference electrode among the plurality of electrodes, with at least two measurement electrodes among the plurality of measurement electrodes of the external accessory.

According to an embodiment, detecting the coupling with the external accessory may include, when a detachable measurement module (e.g., 402 of FIG. 4A) including a communication circuit is coupled to the external accessory, transmitting a signal for sequentially controlling the switching to the detachable measurement module via communication with the detachable measurement module.

According to an embodiment, the method may further include entering a measurement mode for measuring the biometric signal in response to detection of the coupling with the external accessory.

According to an embodiment, the method may further include, when the wearable electronic device includes an optical sensor, measuring an additional biometric signal for the user using at least one light receiving unit and at least one light emitting unit included in the optical sensor and measuring a blood pressure using the measured additional biometric signal.

Figure 8:
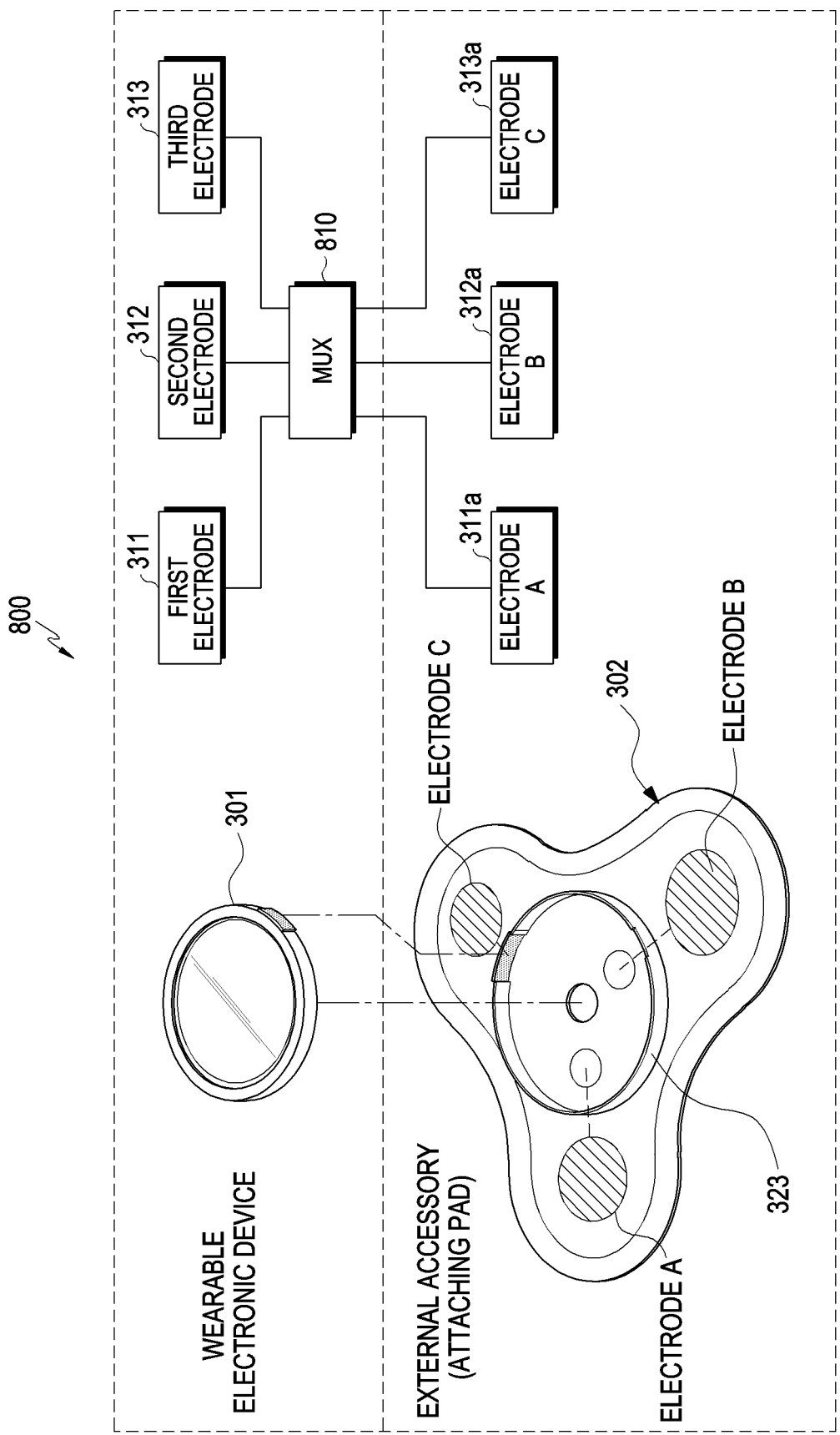
FIG. 8 is a view illustrating a method for selecting an electrode combination in a state where a wearable electronic device is coupled with an external accessory according to an embodiment.

FIG. 8 is a view 800 illustrating a method for selecting an electrode combination, in a state where a wearable electronic device is coupled with an external accessory according to an embodiment.

Referring to FIG. 8, when the wearable electronic device 301 couples with the external accessory including the attaching pad 302, via a coupling member 323, connection between the plurality of measurement electrodes (e.g., electrodes A, B, and C) of the external accessory and the plurality of electrodes (e.g., the first electrode 311, the second electrode 312, and the third electrode 313) of the wearable electronic device 301 may be switched via a MUX 810. In these embodiments, the MUX 810 for switching may be included in the wearable electronic device 301.

According to an embodiment, different electrode combinations for switching may apply depending on whether one of the three electrodes is used as a reference electrode, and whether all of the three electrodes are used without a reference electrode.

For example, when the MUX 810 is used for switching upon using all of the three electrodes without a reference electrode, connection between at least two of the plurality of measurement electrodes (e.g., electrodes A, B, and C) of the external accessory and at least two of the plurality of electrodes (e.g., the first electrode 311, the second electrode 312, and the third electrode 313) of the wearable electronic device 301 may be switched. As such, when all of the three electrodes are used without a reference electrode, all of the plurality of electrodes of the wearable electronic device 301 may be used for switching. For example, switching may be performed so that a pair of electrodes among the plurality of electrodes of the wearable electronic device 301 is connected with a pair of electrodes among the plurality of measurement electrodes of the external accessory.

In contrast, for switching when one of the three electrodes is used as a reference electrode, any one of the plurality of electrodes (e.g., the first electrode 311, the second electrode 312, and the third electrode 313) of the wearable electronic device 301 may be used to apply a reference voltage. For example, when two electrodes are used in the wearable electronic device 301, the remaining two electrodes are used from the plurality of electrodes of the wearable electronic device 301, except for the reference electrode among. Thus, a connection structure may be provided in which the remaining two electrodes electrically contact or connect to the plurality of measurement electrodes (e.g., electrodes A, B, and C) of the external accessory. In such a case, combinations of the remaining electrodes (e.g., the first electrode 311 and the third electrode 313), except for the reference electrode of the wearable electronic device 301, and at least two of the plurality of measurement electrodes (e.g., electrodes A, B, and C) of the external accessory may be sequentially selected and switched. For example, a combination of the first electrode 311 and the third electrode 313 may be sequentially connected to a combination of electrodes A and B, a combination of electrodes B and C, and a combination of electrodes A and C via the MUX 810 and be switched in every predetermined period. By obtaining a measurement signal via a plurality of electrode combinations, biometric signals of the second and third leads, and the first lead, may be obtained, so that biometric information may be obtained precisely and repetitively.

Figure 9:
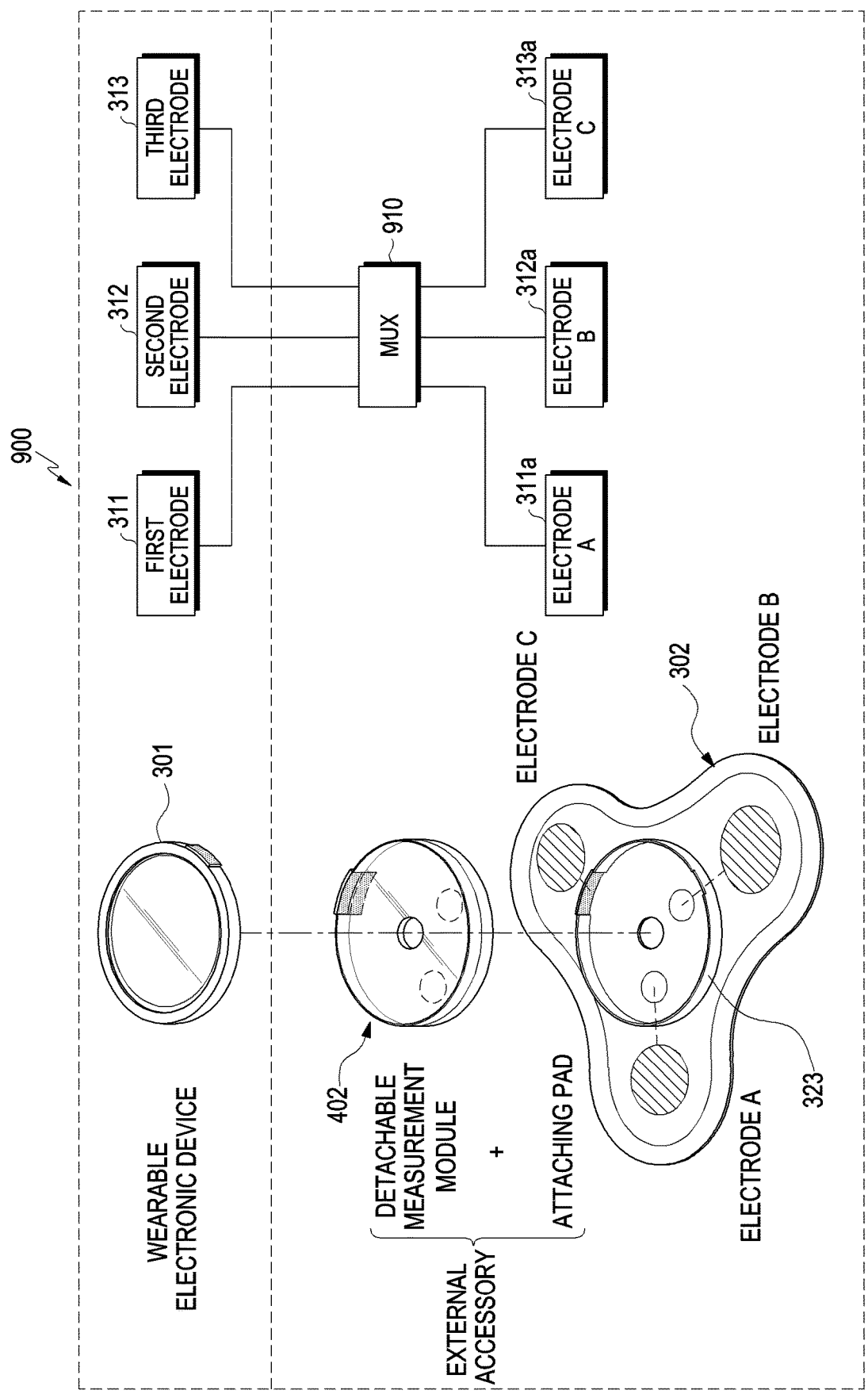
FIG. 9 is a view illustrating a method for selecting an electrode combination in a state where a wearable electronic device establishes communication with an external accessory according to an embodiment.

FIG. 9 is a view 900 illustrating a method for selecting an electrode combination in a state where a wearable electronic device establishes communication with an external accessory according to an embodiment.

Referring to FIG. 9, when the wearable electronic device 301 establishes communication with the external accessory, including the attaching pad 302 and the detachable measurement module 402, connection between the plurality of measurement electrodes (e.g., electrodes A, B, and C) of the external accessory and the plurality of electrodes (e.g., the first electrode 311, the second electrode 312, and the third electrode 313) of the wearable electronic device 301 may be switched via a MUX 910 in the detachable measurement module 402. According to an embodiment, although the same combination of switching as that shown in FIG. 8 applies, switching control via the MUX 910 may be performed by a control signal from the wearable electronic device 301, rather than from a processor in the detachable measurement module 402.

Figure 10:
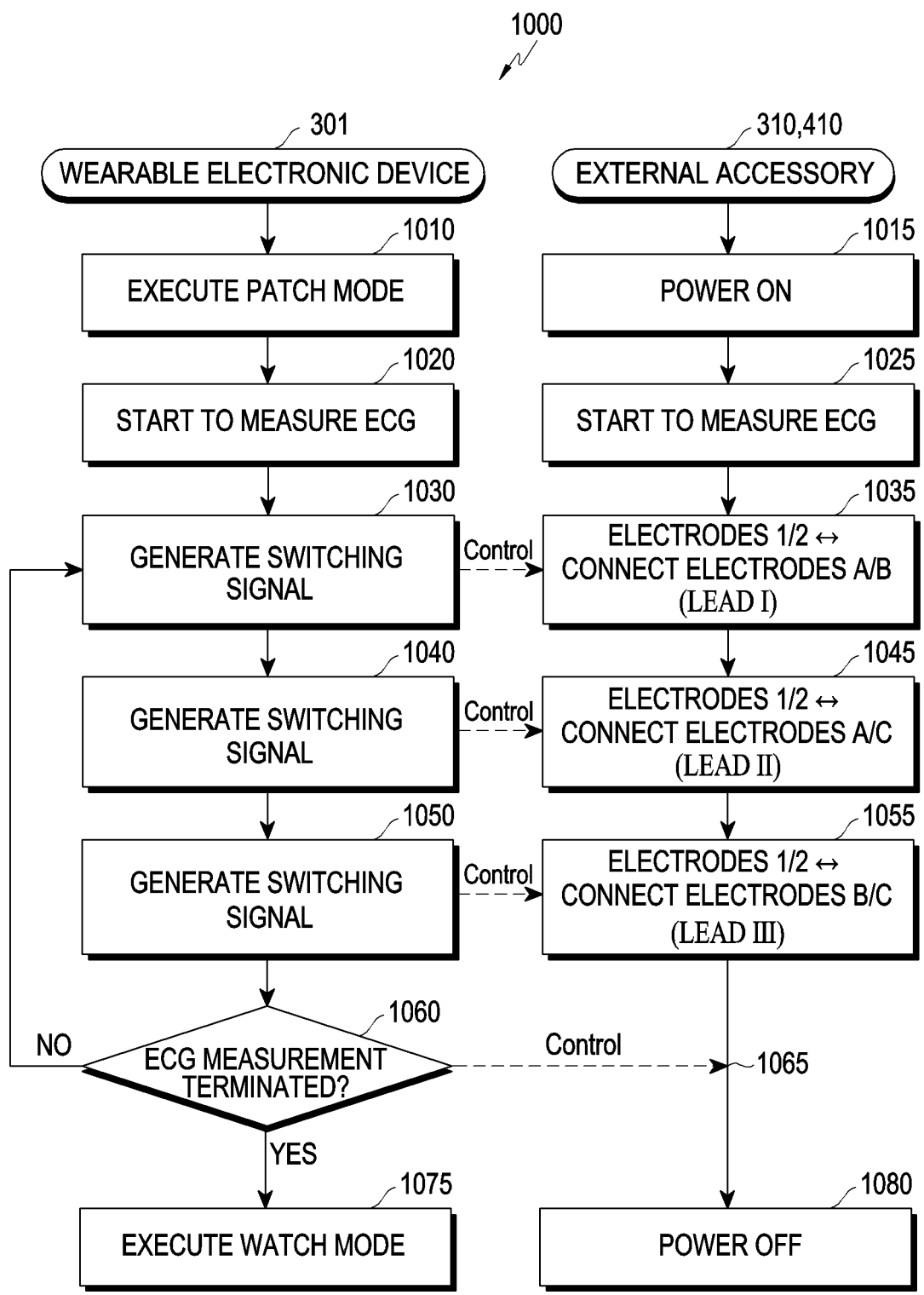
FIG. 10 is a flowchart illustrating operations corresponding to signals transmitted/received between a wearable electronic device and an external accessory according to an embodiment.

FIG. 10 is a flowchart 1000 illustrating operations corresponding to signals transmitted/received between a wearable electronic device and an external accessory according to an embodiment.

Referring to FIG. 10, the wearable electronic device 301 may connect to the external accessory 310 or 410. According to an embodiment, the wearable electronic device 301 may be connected via a coupling structure as shown in FIG. 3, or with the external accessory 310 or 410 via communication connection as shown in FIG. 4A.

When the wearable electronic device 301 connects with the external accessory 310 or 410, the wearable electronic device 301 may execute the patch mode in operation 1010, and may start ECG measurement in operation 1020. According to an embodiment, when the patch mode is executed, the wearable electronic device 301 may deactivate at least one function irrelevant to the measurement of biometric signals, and when connected with the wearable electronic device 301, the external accessory 310 or 410 may power on in operation 1015 and initiate ECG measurement in operation 1025. In this case, the external accessory 310 or 410 may remain attached to the user's body for biometric signal measurement.

Upon successful measurement of ECG, the wearable electronic device 301 may generate a switching signal for controlling the switching of the MUX in operation 1030. In response to the switching signal, a control signal may be transferred to the external accessory 310 or 410. In operation 1035, the external accessory 310 or 410 may connect at least two electrodes (e.g., electrodes 1 and 2) among the plurality of electrodes of the wearable electronic device 301 and at least two electrodes (e.g., electrodes A and B) among the plurality of measurement electrodes of the external accessory 310 or 410 based on the switching signal, thereby forming a first lead.

Subsequently, upon arrival of a predetermined time, e.g., when a measurement period for measuring a second lead arrives, the wearable electronic device 301 may generate a switching signal for controlling the switching of the MUX in operation 1040. In operation 1045, the external accessory 310 or 410 may connect at least two electrodes (e.g., electrodes 1 and 2) among the plurality of electrodes of the wearable electronic device 301 and at least two electrodes (e.g., electrodes A and C) among the plurality of measurement electrodes of the external accessory 310 or 410 based on the switching signal, thereby forming a second lead.

When a next measurement period arrives, the wearable electronic device 301 may generate a switching signal for controlling the switching of the MUX in operation 1050. In operation 1055, the external accessory 310 or 410 may connect at least two electrodes (e.g., electrodes 1 and 2) from among the plurality of electrodes of the wearable electronic device 301, and at least two electrodes (e.g., electrodes B and C) from among the plurality of measurement electrodes of the external accessory 310 or 410 based on the switching signal, thereby forming a third lead. As such, a biometric signal may be measured based on a signal (or voltage difference) detected via the formed lead, or the combination of electrodes configured using at least two electrodes from among the electrodes of the wearable electronic device 301 and the external accessory 310 or 410.

In operation 1060, the wearable electronic device 301 may determine whether the ECG measurement is terminated. If the ECG measurement is not terminated, the wearable electronic device 301 may repeat the above-described operations 1030 to 1050 periodically, according to predetermined time ranges within a total measurement time, thereby obtaining a continuous measurement signal. In operation 1065, the external accessory 310 or 410 may repeat the above-described operations 1025 to 1045 in response to the switching signal from the wearable electronic device 301, until a control signal indicating termination of the ECG measurement is received from the wearable electronic device 301.

Thereafter, when the ECG measurement is terminated, the wearable electronic device 301 may transmit a control signal indicating the termination of the ECG measurement to the external accessory 310 or 410, to thereby release the connection with the external accessory 310 or 410. In operation 1075, the wearable electronic device may execute the watch mode. Here, the watch mode may be a normal mode in which operations are performed on the smart watch. For example, upon switching to the watch mode, at least one function irrelevant to biometric signal measurement, which has been deactivated upon executing the patch mode, may be activated. When the connection with the wearable electronic device 301 is released in response to the control signal according to the ECG measurement termination, the external accessory 310 or 410 may power off in operation 1080.

Figure 11:
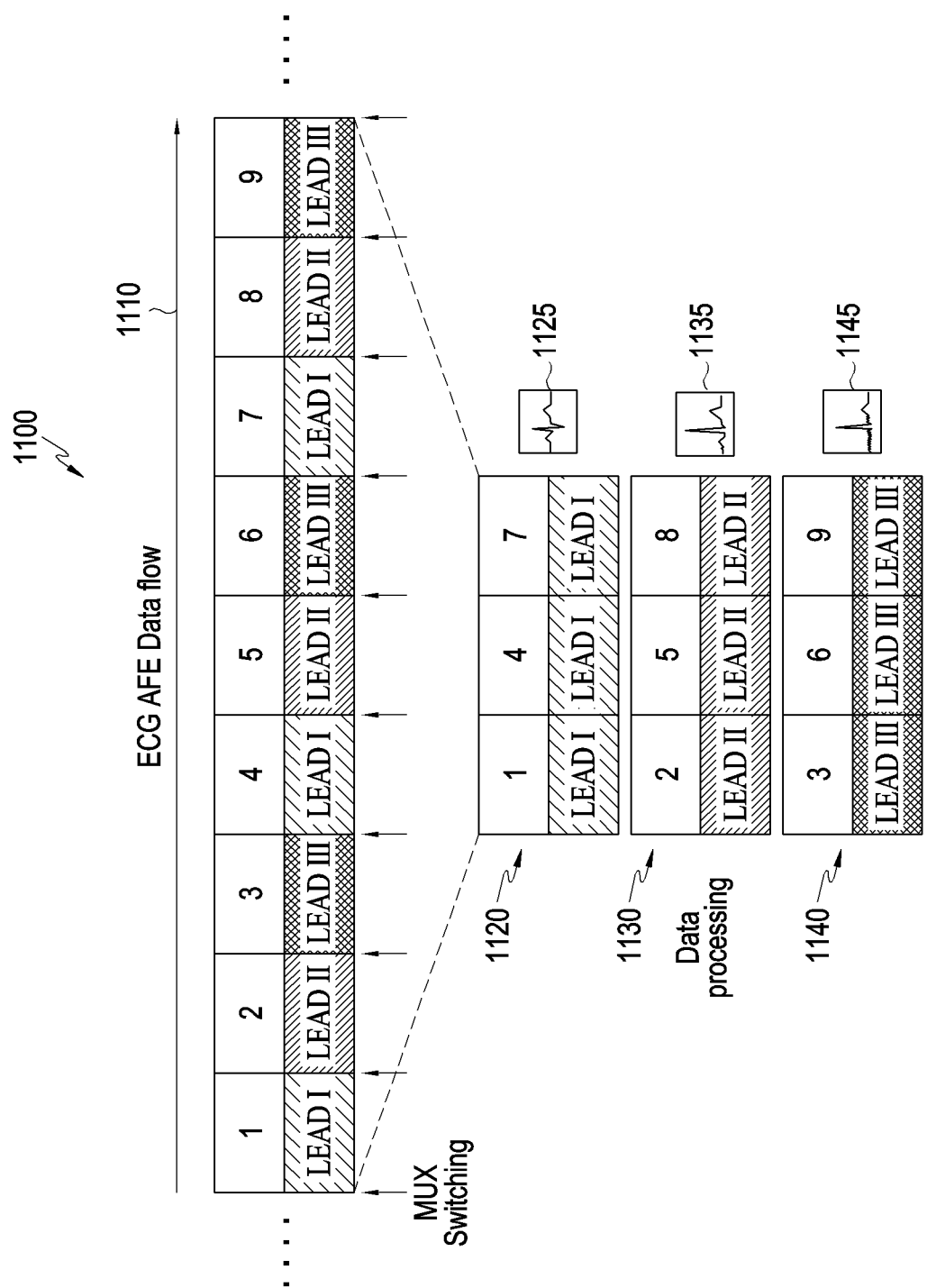
FIG. 11 is a view illustrating a process for obtaining data according to selection of an electrode combination according to an embodiment.

FIG. 11 is a view 1100 illustrating a process for obtaining data according to selection of an electrode combination according to an embodiment. According to an embodiment, an ECG data flow 1110 obtained by a combination of at least two among the plurality of electrodes according to the switching control operation by the wearable electronic device is shown in FIG. 11.

According to an embodiment, when detecting a biometric signal, as the number of electrodes utilized increases, the accuracy of ECG measurement may rise. For example, as the area of each electrode contacting the skin increases, the accuracy of the ECG measurement may also increase. As the number of electrodes increases, the total area of the electrodes contacting the skin increases, and so accuracy increases as well. For example, according to an embodiment, when each of the plurality of electrodes contacts the user's body, two electrodes may be arbitrarily selected to serve as a lead, and the biometric signal may be detected via the selected electrodes. For example, when three electrodes are used for measurement of biometric signals, three electrode combination pairs (e.g., a first lead, a second lead, and a third lead) may be utilized and, as biometric signals are detected via each electrode combination, the detected biometric information may be diversified, resulting in enhancement to the accuracy of the detected biometric information. According to an embodiment, a MUX may be used to select an electrode combination. As the MUX is utilized, a lead may be determined according to the electrode combination as at least two measurement electrodes among the plurality of measurement electrodes of the external accessory connect to at least two electrodes among the plurality of electrodes of the wearable electronic device.

According to an embodiment, when biometric signal measurement is initiated, the wearable electronic device may control switching, thereby connecting a combination of at least two of the plurality of measurement electrodes of the external accessory, with at least two of the plurality of electrodes of the wearable electronic device using the MUX in predetermined time units. According to an embodiment, the wearable electronic device may execute switching to connect at least two electrodes from among the plurality of electrodes (e.g., electrodes 1, 2, and 3) of the wearable electronic device, with at least two measurement electrodes from among the plurality of measurement electrodes (e.g., electrodes A, B, and C) of the external accessory via the MUX. To obtain a biometric reading that is accurate when repeated during continuous monitoring of the biometric signals, the wearable electronic device may change the combinations of which two measurement electrodes from among the measurement electrodes of the external accessory attached to the user's body, and which two electrodes from among the electrodes of the wearable electronic device, thereby setting different combinations of electrodes as leads. For example, when at least two electrodes (e.g., electrodes 1 and 2) among the plurality of electrodes (e.g., electrodes 1, 2, and 3) of the wearable electronic device are connected with at least two measurement electrodes (e.g., electrodes A and B) among the plurality of measurement electrodes (e.g., electrodes A, B, and C) of the external accessory via the MUX according to switching order, the first lead (Lead I) may be set, when at least two electrodes (e.g., electrodes 1 and 2) are connected with at least two measurement electrodes (e.g., electrodes A and C), the second lead (Lead II) may be set, and when at least two electrodes (e.g., electrodes 1 and 2) are connected with at least two measurement electrodes (e.g., electrodes B and C), the third lead (Lead III) may be set.

As shown in FIG. 11, the biometric signal continuously monitoring may be ECG data sequentially obtained in the order of the first lead (Lead I), the second lead (Lead II), and the third lead (Lead III), as different electrode combinations are connected according to the MUX switching. The ECG data may be divided into the first lead (Lead I) 1120, the second lead (Lead II) 1130, and the third lead (Lead III) 1140 according to the control timing for recording and be stored in the memory (e.g., 530 of FIG. 5).

According to an embodiment, the wearable electronic device may obtain the aVF, aVL, and aVR signals based on the combination of the measured first lead (Lead I) 1120, second lead (Lead II) 1130, and third lead (Lead III) 1140 data. For example, the wearable electronic device may obtain the aVF, aVL, and aVR signals based on Equation 1 below.

$aVL = (\text{Lead } I - \text{Lead } III)/2$ $-aVR = (\text{Lead } I + \text{Lead } II)/2$ $aVF = (\text{Lead } II + \text{Lead } III)$ [Equation 1]

Referring to Equation 1, aVL may denote the potential difference measured between the center of the heart and the left wrist (LA), aVR may denote the potential difference measured between the center of the heart and the right wrist (RA), and aVF may denote the potential difference measured between the center of the heart and the left ankle (LF).

Figure 12:
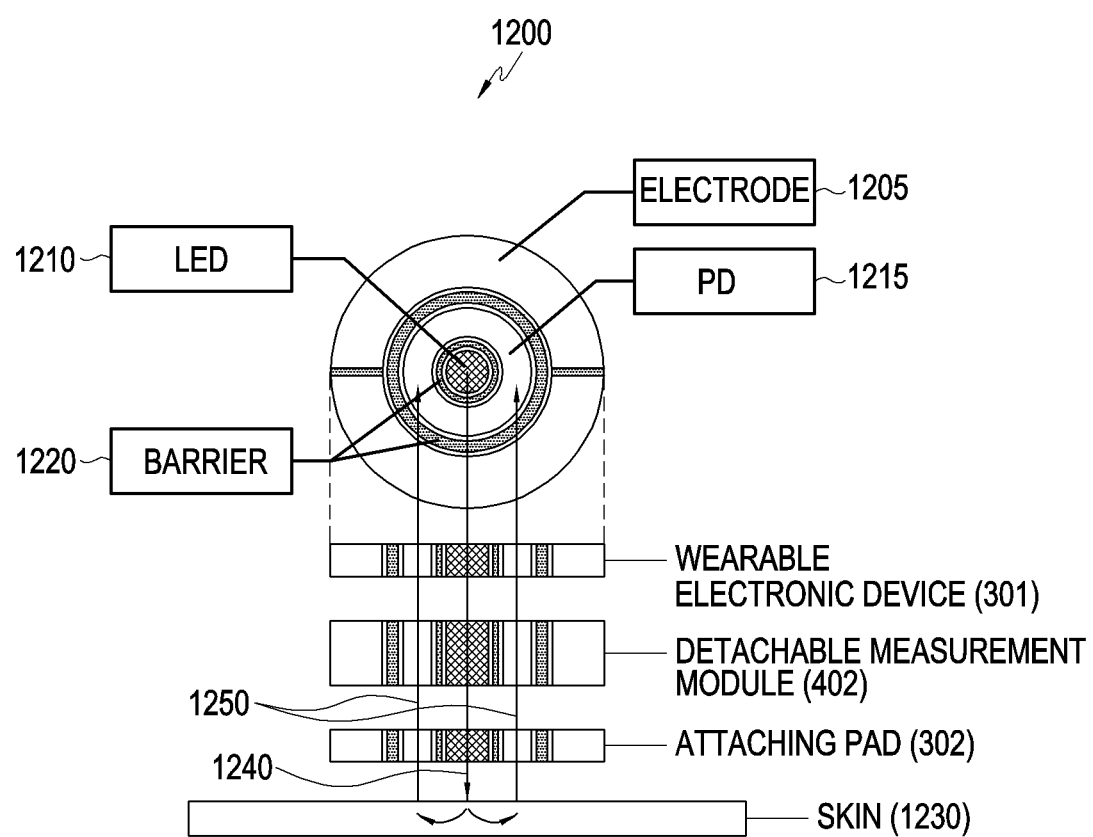
FIG. 12 is a view illustrating a structure for measuring a PPG signal according to an embodiment.

FIG. 12 is a view 1200 illustrating a structure for measuring a PPG signal according to an embodiment.

Referring to FIG. 12, a wearable electronic device may include a plurality of sensors, and may measure a PPG signal (or data) using a PPG sensor, which is an optical sensor, from among the plurality of sensors. FIG. 12 illustrates a rear surface of the wearable electronic device 301 and a cross section of each of the wearable electronic device 301, the detachable measurement module 402, and the attaching pad 302.

According to an embodiment, in the surface receiving coupling of the wearable electronic device 301, openings may be formed in the detachable measurement module 402 and in the attaching pad 302, at positions corresponding to the PPG sensor (e.g., the PPG sensor 315 of FIG. 3), which may be mounted on the rear surface of the wearable electronic device 301, such that the cross section of the attaching pad 302 may correspond to a cross section of the opening. According to an embodiment, PPG signals may be gathered simultaneously with ECG signal measurement via the middle hole, which is divided by a barrier in the opening of each of the detachable measurement module 402 and the attaching pad 302, corresponding to the positions of at least light emitting unit (LED) 1210 and at least one light receiving unit (PD) 1215. According to an embodiment, when the wearable electronic device 301 is coupled with the attaching pad 302, the detachable measurement module 402 may be omitted.

According to an embodiment, at least one electrode 1205, at least one light emitting unit (LED) 1210, and at least one light receiving unit (PD) 1215 may be included on the rear surface of the wearable electronic device 301, and the at least one light receiving unit 1215 may include an opaque optical shield (e.g., the barrier) 1220 surrounding the side portion thereof. The opaque optical shield may be referred to as a barrier, and may define a path for receiving the reflected light.

According to an embodiment, when measurement is initiated, the light from at least one light emitting unit (LED) 1210 may be oriented (1240) to the user's skin 1230, and the reflected light may be modulated by the blood flow under the user's skin 1230. The reflected light may be received (1250) by at least one light receiving unit (PD) 1215 via the path formed by the barrier structure 1220.

According to an embodiment, when measurement is initiated, the wearable electronic device 301 may obtain an ECG signal based on the signals from the measurement electrodes of the attaching pad contacting the user's body, which includes the at least one electrode 1205 that is electrically connected with the connection terminal of the detachable measurement module 402, or the connection terminal of the attaching pad 302. While measuring the ECG signal, an additional biometric signal for the user may be measured using at least one light emitting unit 1210 and at least one light receiving unit 1215 included in the PPG sensor, which is an optical sensor. The additional biometric signal measured may be used to measure the blood pressure, which is described below in detail with reference to FIG. 13.

Figure 13:
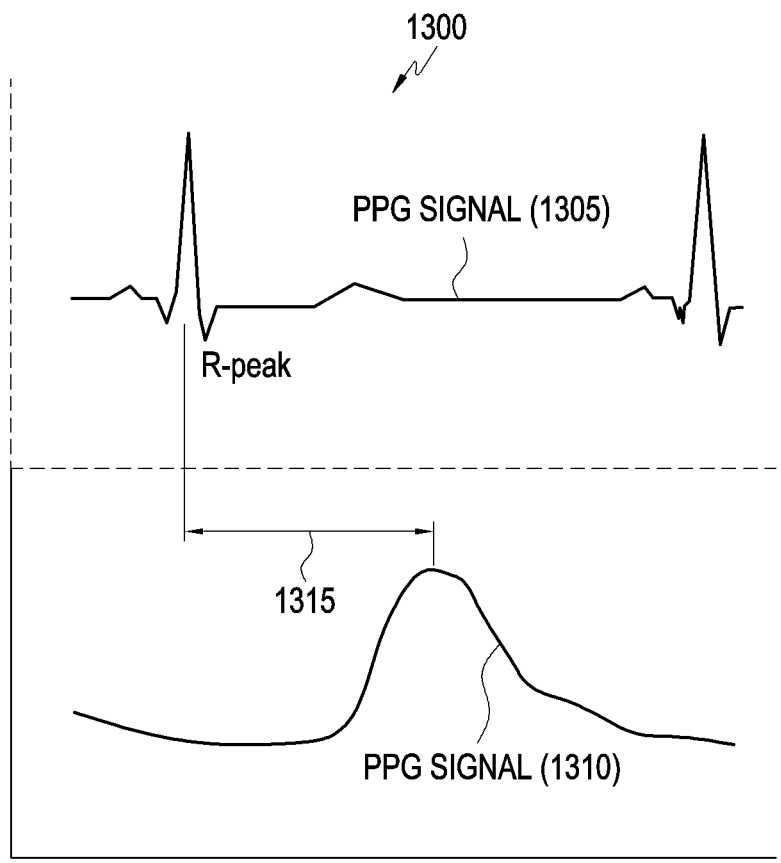
FIG. 13 is a view illustrating a PTT measurement method using an ECG signal and a PPG signal according to an embodiment.

FIG. 13 is a view 1300 illustrating a PTT measurement method using an ECG signal and a PPG signal according to an embodiment.

According to an embodiment, an ECG signal 1305 and a PPG signal 1310 may be measured by the ECG sensor and PPG sensor, respectively, in the wearable electronic device. The phase delay 1315 may be measured by extracting feature points from the two signals and using a difference in position (or difference in time) between the two signals. For example, the phase delay may be measured using a difference in time between the peak of the PPG signal 1310 obtained by the PPG sensor, e.g., the peak of the pulse wave, and the peak of the pattern of the ECG signal obtained by the ECG sensor. When the phase delay is measured, the blood pressure may be estimated based on pulse wave velocity (PWV) and the relationship between pulse wave velocity (PWV) and blood pressure, allowing an estimate of blood pressure to be output.

For example, PWV denotes the propagation speed of blood velocity pulses or pressure pulses along the artery due to the contraction of the left ventricle of the heart. The PWV may be obtained by measuring the difference in pulse transit time (PTT) between two points on the arterial pathway, the distances of which are known. The PTT may be defined as a time taken for the pulsating pressure wave to be transmitted from the aortic valve to the peripheral site, and the PWV may be inversely proportional to the PTT. Therefore, an increase or decrease in the PTT reflects a decrease or increase in the PWV, and represents the characteristics of the entire section from the heart to the peripheral artery. Since the PWV represents blood vessel-dependent characteristics, the blood measurement value may be provided via a predetermined equation. For example, the PWV may be calculated by the predetermined equation, e.g., (PWV=D/Dt, cm/sec), i.e., by dividing the distance (D) between two points from the heart to the peripheral or from the peripheral to the heart by the utilized time (Dt).

According to an embodiment, the wearable electronic device may measure the degree of percutaneous oxygen saturation (SpO2) using the same optical method as the PPG sensor. When the plurality of sensors included in the wearable electronic device are used as described above, it is possible to provide health information based on complex biometric information as well as current health conditions such as ECG and blood pressure.

Figure 14:
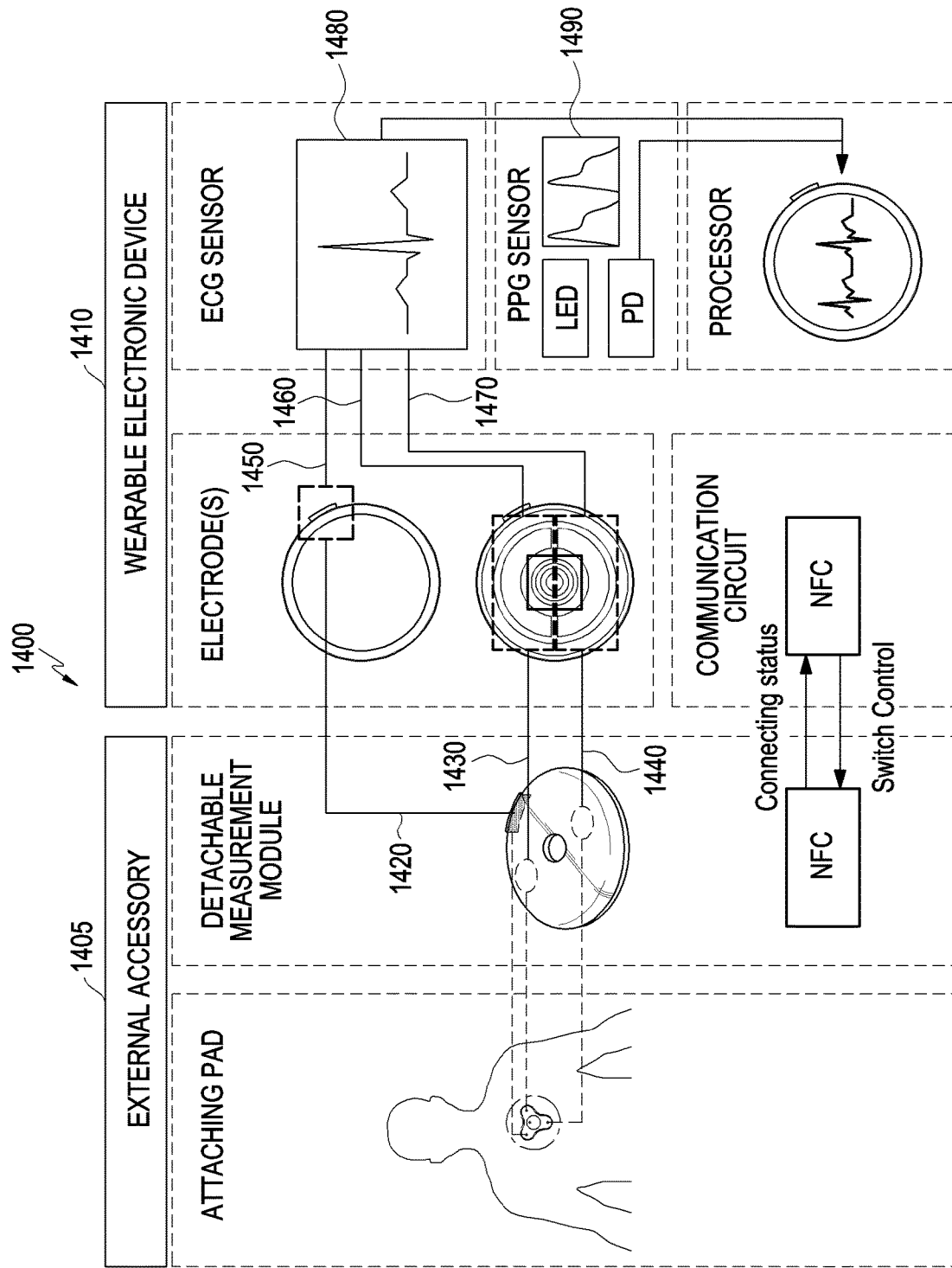
FIG. 14 is a view illustrating a detailed configuration of an entire system including a external accessory and a wearable electronic device for biometric signal measurement, according to an embodiment.

FIG. 14 is a view 1400 illustrating a detailed configuration of an entire system including an external accessory and a wearable electronic device for biometric signal measurement, according to an embodiment.

According to an embodiment, an overall system for biometric signal measurement may include an external accessory 1405 (e.g., the external accessory 310 of FIG. 3) attached to the user's body, and a wearable electronic device 1410 (e.g., the wearable electronic device 301 of FIG. 3) for obtaining a biometric signal via connection with the external accessory 1405.

Referring to FIG. 14, the wearable electronic device 1410 may be connected via a detachable measurement module and a communication circuit 690, e.g., NFC communication circuitry, and may transmit signals for switching control.

According to an embodiment, when the wearable electronic device 1410 couples with an attaching pad, the plurality of electrodes of the attaching pad may respectively correspond to the electrodes of the wearable electronic device. According to an embodiment, when the wearable electronic device 1410 establishes communication via the detachable measurement module, the electrodes of the wearable electronic device may be connected (1420, 1430, and 1440) via the connection terminals of the detachable measurement module.

For example, the electrodes A, B, and C of the attaching pad may connected with the electrodes (e.g., the first electrode, the second electrode, and the third electrode), respectively, of the wearable electronic device 1410 via the detachable measurement module, or by some other mechanism without a detachable measurement module. Thus, signals may be obtained via a combination of at least two of the paths of the electrode combinations 1450, 1460, and 1470 from the electrodes (e.g., the first electrode, the second electrode, and the third electrode) of the wearable electronic device 1410.

According to an embodiment, at least two electrodes may be selected from among the plurality of electrodes (e.g., the first electrode, the second electrode, and the third electrode) of the wearable electronic device, for connection with at least two electrodes from among the plurality of measurement electrodes of the external accessory. Taken together, three combination pairs may be possible. In such a case, a first electrode combination 1450 and 1460, a second electrode combination 1450 and 1470, and a third electrode combination 1460 and 1470 may be utilized as possible examples.

According to an embodiment, at least two electrodes may be selected from among the plurality of electrodes (e.g., the first electrode, the second electrode, and the third electrode) of the wearable electronic device, for connection with at least two electrodes selected from among the plurality of electrodes of the external accessory. When any one of the plurality of electrodes (e.g., the first electrode, the second electrode, and the third electrode) is used as a reference electrode, the electrode combinations may be sequentially selected, excepting the reference electrode. In such a case, when the third electrode combination 1460 and 1470 is used as a reference electrode as an example, the first electrode combination 1450 and 1460 and the second electrode combination 1450 and 1470 may be utilized as the electrode combination.

As described above, the wearable electronic device may obtain the biometric information 1490 by the PPG signal based on the PPG sensor or the biometric information 1480 by the ECG signal based on the voltage difference between at least two electrodes among the plurality of measurement electrodes of the external accessory.

Figure 15:
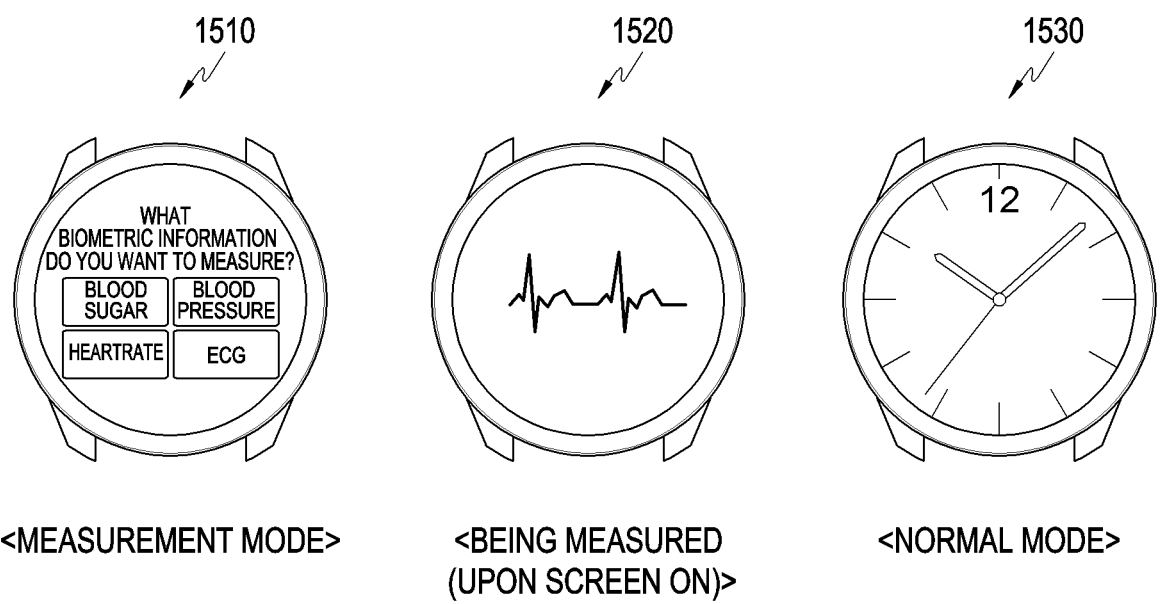
FIG. 15 is a view illustrating an example user interface in a wearable electronic device according to an embodiment.

FIG. 15 is a view illustrating an example user interface in a wearable electronic device according to an embodiment. FIG. 15 illustrates an example user interface that changes depending on variations in mode on the wearable electronic device.

According to an embodiment, as in a first screen 1510, the wearable electronic device (e.g., the wearable electronic device 301 of FIG. 3) may display a menu related to biometric measurement on the display, before starting the measurement mode (e.g., the patch mode). For example, the wearable electronic device may display selectable options for biometric readings, such as blood sugar, blood pressure, heart rate and ECG on the display. As described above, the wearable electronic device may provide the menu to permit a user to select the biometric information to be measured.

According to an embodiment, in a second screen 1520, the wearable electronic device may display a screen for indicating measurement is underway after switching to the measurement mode. In the measurement mode, functions irrelevant to biometric information measurement may be restricted and/or terminated. For example, non-biometric functions maybe limited or restricted, such as disabling deactivation of the communication function, switching display modes, or adjusting display configuration (e.g., brightness adjustment). Further, allowable inputs may be restricted to prevent user error while biometric measurements are being performed. For example, touch input to the screen may be restricted to prevent malfunction during measurement, with physical keys operated or some areas on the display touchable.

According to an embodiment, the screen of the wearable electronic device may be deactivated simultaneously with the initiation of biometric measurement. In another embodiment, a second screen 1520 indicating that measurement is underway may be displayed during reception of a user input during measuring (such as depressing of a physical key) during biometric measurement. Further, previously measured information may be displayed during biometric measurement. When the biometric measurement is complete, the wearable electronic device may display a screen including the results of the biometric measurement, including graphical elements (e.g., graph) and/or letters (e.g., numbers or states) indicating the measured biometric information.

According to an embodiment, as in a third screen 1530, the wearable electronic device may display an original screen, e.g., the watch screen, on the display when the biometric measurement mode is terminated. For example, the wearable electronic device may re-activate the functions which have been deactivated or restricted as irrelevant to biometric measurement.

The electronic device according to certain embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

There is provided a storage medium storing instructions, the instructions configured to be executed by at least one processor to enable the at least one processor to perform at least one operation, the at least one operation including detecting a coupling with an external accessory contacting a user's body and measuring a biometric signal based on a voltage received via at least two measurement electrodes among a plurality of measurement electrodes included in the external accessory, in response to detection of the coupling.

As is apparent from the foregoing description, according to certain embodiments, a wearable electronic device may be configured to be detachable from an external accessory including an attaching pad and may thus remain in the stable coupling state, increasing the accuracy of biometric signal measurement.

According to certain embodiments, as an external accessory including an attaching pad and a detachable measurement module establishes communication with a wearable electronic device, it is possible to monitor more data, such as of second and third leads, as well as the first lead (lead I) formed by both arms.

According to certain embodiments, a wearable electronic device may increase the accuracy and reliability of biometric signal measurement using an external accessory and may measure biometric signals with various characteristics, such as blood pressure and sleep apnea, using various sensors, thus saving costs for purchasing a separate medical device.

The embodiments herein are provided merely for better understanding of the disclosure, and the disclosure should not be limited thereto or thereby. It should be appreciated by one of ordinary skill in the art that various changes in form or detail may be made to the embodiments without departing from the disclosure defined by the following claims.

What is claimed is:

1. A wearable electronic device, comprising:
   at least one sensor including a plurality of electrodes, wherein a first electrode is disposed on a side surface of the wearable electronic device, and a second electrode is disposed on a bottom surface of the wearable electronic device;
   at least one processor operatively connected with the at least one sensor; and
   a memory operatively connected with the at least one processor, wherein the memory stores instructions executable by the at least one processor to cause the wearable electronic device to:
   detect coupling of the wearable electronic device with an external accessory configured to contact a body of a user, wherein the external accessory includes a pad body and a receiving wall extending vertically from the pad body so as to form an opening for coupling to the wearable electronic device, a first connection terminal disposed on the receiving wall so as to contact the first electrode disposed on the side surface, and a second connection terminal disposed on a base of the opening so as to contact the second electrode disposed on the bottom surface, when the wearable electronic device is coupled to the external accessory, and
   based on detecting the coupling of the wearable electronic device with the external accessory, measure a biometric signal using voltages received from at least two measurement electrodes from among a plurality of measurement electrodes included in the external accessory.

2. The wearable electronic device of claim 1, wherein the wearable electronic device further includes a photoplethysmography (PPG) sensor exposed through a central portion of the bottom surface,
   wherein the external accessory includes a hole formed at a central portion of the base of the opening, such that light emitted from the PPG sensor reaches skin through the hole when the wearable electronic device is coupled to the external accessory,
   wherein the external accessory includes an attaching pad,
   wherein the plurality of measurement electrodes are included in the attaching pad, and
   wherein the attaching pad is detachably coupled to one surface of a housing of the wearable electronic device.

3. The wearable electronic device of claim 2, wherein the plurality of electrodes are arranged to be exposed to an external environment of the wearable electronic device, and
   wherein the coupling with the external accessory is detected when the plurality of electrodes of the at least one sensor electrically couples to the plurality of measurement electrodes included in the attaching pad via a first connection terminal.

4. The wearable electronic device of claim 3, wherein one of the plurality of electrodes included in the at least one sensor is designated as a reference electrode, and the instructions are executable to cause the processor to:
   sequentially control switching for connecting of at least two electrodes from among the plurality of electrodes with at least two corresponding electrodes from among the plurality of measurement electrodes of the external accessory,
   wherein the reference electrode is excepted from the switching.

5. The wearable electronic device of claim 4, wherein the biometric signal is measured in response to the switching, and
   wherein the received voltage is generated from the connection of the at least two electrodes from among the plurality of electrodes of the at least one sensor, with the at least two electrodes from among the plurality of measurement electrodes of the external accessory, and
   wherein the connection is created through the attaching pad via the first connection terminal.

6. The wearable electronic device of claim 4, wherein the instructions are further executable to enable the at least one processor to:
   detecting coupling of a detachable measurement module including a communication circuit to the external accessory,
   based on detecting coupling of the detachable measurement module, transmit a signal to the detachable measurement module for sequentially controlling the switching.

7. The wearable electronic device of claim 6, wherein the detachable measurement module includes a second connection terminal to allow electrical connection between the plurality of measurement electrodes included in the attaching pad with the plurality of electrodes of the wearable electronic device, and
   wherein the detachable measurement module includes a coupler configured to couple to the wearable electronic device.

8. The wearable electronic device of claim 3, wherein the instructions are executable to cause the at least one processor to:
   sequentially control switching for connecting at least two electrodes from among the plurality of electrodes included in the at least one sensor, with at least two measurement electrodes from among the plurality of measurement electrodes of the external accessory.

9. The wearable electronic device of claim 1, wherein the instructions are executable to cause the at least one processor to: based on detecting coupling with the external accessory, execute a measurement mode for measuring the biometric signal.

10. The wearable electronic device of claim 9, wherein the instructions are executable to cause the at least one processor to: upon executing the measurement mode, deactivate one or more functions unrelated to measurement of the biometric signal.

11. The wearable electronic device of claim 1, wherein the at least one sensor includes an optical sensor including at least one light receiving unit and at least one light emitting unit, and
wherein the instructions are executable to cause the at least one processor to:
measure an additional biometric signal using the at least one light receiving unit and the at least one light emitting unit, and measure a blood pressure of the user using the measured additional biometric signal.

12. A method for processing a biometric signal in a wearable electronic device, the method comprising:
detecting a coupling of the wearable electronic device with an external accessory configured to contact a body of a user, wherein the external accessory includes a pad body and a receiving wall extending vertically from the pad body so as to form an opening for coupling to the wearable electronic device, a first connection terminal disposed on the receiving wall so as to contact a first electrode of the wearable electronic device disposed on a side surface thereof, and a second connection terminal disposed on a base of the opening so as to contact a second electrode of the wearable electronic device disposed on a bottom surface thereof, when the wearable electronic device is coupled to the external accessory; and
based on detecting the coupling of the wearable electronic device with the external accessory, measuring a biometric signal using voltages received from at least two measurement electrodes from among a plurality of measurement electrodes included in the external accessory.

13. The method of claim 12, wherein the wearable electronic device further includes a photoplethysmography (PPG) sensor exposed through a central portion of the bottom surface,
wherein the external accessory includes a hole formed at a central portion of the base of the opening, such that light emitted from the PPG sensor reaches skin through the hole when the wearable electronic device is coupled to the external accessory,
wherein the external accessory includes an attaching pad,
wherein the plurality of measurement electrodes are included in the attaching pad, and
wherein the attaching pad is detachably coupled to one surface of a housing of the wearable electronic device.

14. The method of claim 12, wherein the wearable electronic device further includes a plurality of electrodes which are arranged to be exposed to an external environment of the wearable electronic device, and
wherein the coupling with the external accessory is detected when the plurality of electrodes of at least one sensor of the wearable electronic device electrically couples to the plurality of measurement electrodes included in an attaching pad of the external accessory via a first connection terminal.

15. The method of claim 14, wherein measuring the biometric signal further includes sequentially controlling, periodically based on a predetermined time, switching for connecting at least two electrodes from among the plurality of electrodes of the wearable electronic device, with at least two measurement electrodes from among the plurality of measurement electrodes of the external accessory.

16. The method of claim 15, wherein one of the plurality of electrodes included in at least one sensor of the wearable electronic device is designated as a reference electrode, and
wherein the reference electrode is excepted from the switching.

17. The method of claim 12, further comprising:
detecting coupling of a detachable measurement module including a communication circuit to the external accessory,
based on detecting coupling of the detachable measurement module, transmitting a signal to the detachable measurement module for sequentially controlling the switching.

18. The method of claim 12, further comprising:
based on detecting coupling with the external accessory, executing a measurement mode for measuring the biometric signal.

19. The method of claim 12, wherein the at least one sensor of the wearable electronic device includes an optical sensor including at least one light receiving unit and at least one light emitting unit,
the method further comprising:
measuring an additional biometric signal using the at least one light receiving unit and the at least one light emitting unit included in the optical sensor; and
measuring a blood pressure using the measured additional biometric signal.

20. A non-transitory storage medium storing instructions, the instructions configured to be executed by at least one processor to enable the at least one processor to perform at least one operation in a wearable electronic device, the at least one operation comprising:
detecting a coupling of a wearable electronic device with an external accessory configured to contact a user's body, wherein the external accessory includes a pad body and a receiving wall extending vertically from the pad body so as to form an opening for coupling to the wearable electronic device, a first connection terminal disposed on the receiving wall so as to contact a first electrode of the wearable electronic device disposed on a side surface thereof, and a second connection terminal disposed on a base of the opening so as to contact a second electrode of the wearable electronic device disposed on a bottom surface thereof, when the wearable electronic device is coupled to the external accessory; and
based on detecting the coupling of the wearable electronic device with the external accessory, measuring a biometric signal using a voltage received from at least two measurement electrodes from among a plurality of measurement electrodes included in the external accessory.

* * * * *